US012427040B2

(12) United States Patent
Benning

(10) Patent No.: US 12,427,040 B2
(45) Date of Patent: *Sep. 30, 2025

(54) PROSTHETIC DIGIT WITH ARTICULATING LINKS

(71) Applicant: Touch Bionics Limited, Livingston (GB)

(72) Inventor: Matthew James Benning, Livingston (GB)

(73) Assignee: Touch Bionics Limited, Livingston (GB)

( * ) Notice: Subject to any disclaimer, the term of this patent is extended or adjusted under 35 U.S.C. 154(b) by 816 days.

This patent is subject to a terminal disclaimer.

(21) Appl. No.: 17/602,247

(22) PCT Filed: Apr. 8, 2020

(86) PCT No.: PCT/IB2020/053373
§ 371 (c)(1),
(2) Date: Oct. 7, 2021

(87) PCT Pub. No.: WO2020/208557
PCT Pub. Date: Oct. 15, 2020

(65) Prior Publication Data
US 2022/0160521 A1    May 26, 2022

Related U.S. Application Data

(60) Provisional application No. 62/832,166, filed on Apr. 10, 2019.

(51) Int. Cl.
*A61F 2/70*    (2006.01)
*A61F 2/54*    (2006.01)
(Continued)

(52) U.S. Cl.
CPC ............ *A61F 2/586* (2013.01); *A61F 2/70* (2013.01); *B25J 15/0009* (2013.01);
(Continued)

(58) Field of Classification Search
None
See application file for complete search history.

(56) References Cited

U.S. PATENT DOCUMENTS

| 760,102 A | 5/1904 | Carnes |
| 1,253,823 A | 1/1918 | Hobbs |

(Continued)

FOREIGN PATENT DOCUMENTS

| CN | 1803413 | 7/2006 |
| CN | 100 336 639 | 9/2007 |

(Continued)

OTHER PUBLICATIONS

Amended Complaint for Patent Infringement in 166 pages filed by Vincent Systems GmbH, dated Apr. 15, 2020, in the lawsuit of *Vincent Systems GmbH v. Össur hf. and Össur Americas, Inc.* (collectively "Össur"), in the United States District Court, Central District of California, Case No. 8:19-VC-02157 JLS (DFMx), including Exhibits A-J. The Amended Complaint and the accompanying Exhibits include information regarding Össur's products that were on sale prior to the Apr. 10, 2019 priority date of the present application and were accused of infringement. Applicant requests that the Examiner consider the information describing details of Össur's products to have been described in a printed publication, or in public use, on sale, or otherwise available to the public, prior to the Apr. 10, 2019 priority date of the present application.

(Continued)

*Primary Examiner* — David H Willse
(74) *Attorney, Agent, or Firm* — Knobbe Martens Olson & Bear, LLP

(57) ABSTRACT

Features for prosthetic digits are described. The digits mimic natural fingers by having multiple articulating segments, for example three, that can rotate varying amounts. Rotatable and/or linearly expandable mechanical links are configured to provide the digit segments with multiple degrees of rotational freedom. The digit may have an actuator that outputs linear actuation to cause rotation of the digit segments. The digit may have an expandable proximal link to allow for variable relative rotational positions of the segments. Middle and/or distal digit segments may fully rotate independent of rotation of a proximal digit segment. The rotated digit may thus fully surround and grasp small or large objects, objects with irregular outer contours, etc.

22 Claims, 16 Drawing Sheets

(51) Int. Cl.
    *A61F 2/58*     (2006.01)
    *B25J 15/00*     (2006.01)
    *B25J 15/02*     (2006.01)
    *B25J 15/10*     (2006.01)
    *B25J 15/12*     (2006.01)
    *A61F 2/50*     (2006.01)
    *A61F 2/68*     (2006.01)
    *A61F 2/76*     (2006.01)

(52) U.S. Cl.
    CPC ... *B25J 15/0293* (2013.01); *A61F 2002/5038* (2013.01); *A61F 2002/5073* (2013.01); *A61F 2002/587* (2013.01); *A61F 2002/6836* (2013.01); *A61F 2002/701* (2013.01); *A61F 2002/7615* (2013.01)

(56) References Cited

U.S. PATENT DOCUMENTS

| | | |
|---|---|---|
| 1,507,683 A | 9/1924 | Pecorella et al. |
| 2,445,711 A | 7/1948 | Fitch |
| 2,477,463 A | 7/1949 | Otterman |
| 2,549,716 A | 4/1951 | Simpson |
| 2,586,293 A | 2/1952 | Birkigt |
| 2,592,842 A | 4/1952 | Alderson |
| 2,669,727 A | 2/1954 | Opuszenski |
| 2,983,162 A | 5/1961 | Musser |
| 3,509,583 A | 5/1970 | Fraioli |
| 3,582,857 A | 6/1971 | Kishel |
| 3,641,832 A | 2/1972 | Shigeta et al. |
| 3,683,423 A | 8/1972 | Crapanzano |
| 3,700,845 A | 10/1972 | Jonsson |
| 3,751,995 A | 8/1973 | Carlson |
| 3,837,010 A | 9/1974 | Prout |
| 3,866,246 A | 2/1975 | Seamone et al. |
| 3,883,900 A | 5/1975 | Jerard et al. |
| 3,922,930 A | 12/1975 | Fletcher et al. |
| 3,983,986 A | 10/1976 | Allard |
| 4,044,274 A | 8/1977 | Ohm |
| 4,084,267 A | 4/1978 | Zadina |
| 4,094,016 A | 6/1978 | Eroyan |
| 4,114,464 A | 9/1978 | Schubert et al. |
| 4,398,110 A | 8/1983 | Flinchbaugh et al. |
| 4,558,704 A | 12/1985 | Petrofsky |
| 4,565,457 A | 1/1986 | Flander |
| 4,577,127 A | 3/1986 | Ferree et al. |
| 4,623,354 A | 11/1986 | Childress et al. |
| 4,660,702 A | 4/1987 | Flotow |
| 4,678,952 A | 7/1987 | Peterson et al. |
| 4,808,187 A | 2/1989 | Patterson et al. |
| 4,813,303 A | 3/1989 | Beezer et al. |
| 4,822,238 A | 4/1989 | Kwech |
| 4,946,380 A | 8/1990 | Lee |
| 4,955,918 A | 9/1990 | Lee |
| 4,990,162 A | 2/1991 | LeBlanc et al. |
| 5,062,673 A | 11/1991 | Mimura |
| 5,413,611 A | 5/1995 | Haslam, II et al. |
| 5,501,498 A | 3/1996 | Ulrich |
| 5,581,166 A | 12/1996 | Eismann et al. |
| 5,605,071 A | 2/1997 | Buchanan, Jr. |
| 5,888,246 A * | 3/1999 | Gow ............... A61F 2/583 623/64 |
| 6,223,615 B1 | 5/2001 | Huck |
| 6,344,062 B1 | 2/2002 | Abboudi et al. |
| 6,361,570 B1 | 3/2002 | Gow |
| 6,517,132 B2 | 2/2003 | Matsuda et al. |
| 6,591,707 B2 | 7/2003 | Torii et al. |
| 6,660,043 B2 | 12/2003 | Kajitani et al. |
| 6,786,112 B2 | 9/2004 | Ruttor |
| 6,846,331 B2 | 1/2005 | Senoir |
| 6,896,704 B1 | 5/2005 | Higuchi et al. |
| 6,908,489 B2 | 6/2005 | Didrick |
| 6,918,622 B2 | 7/2005 | Kim et al. |
| 7,041,141 B2 | 5/2006 | Iversen et al. |
| 7,243,569 B2 | 7/2007 | Takahashi et al. |
| 7,316,304 B2 | 1/2008 | Heravi et al. |
| 7,370,896 B2 | 5/2008 | Anderson et al. |
| 7,481,782 B2 | 1/2009 | Scott et al. |
| 7,655,051 B2 | 2/2010 | Stark |
| 7,823,475 B2 | 11/2010 | Hirabayashi et al. |
| 7,867,287 B2 | 1/2011 | Puchhammer |
| 7,922,773 B1 | 4/2011 | Kuiken |
| 8,052,185 B2 | 11/2011 | Madhani |
| 8,100,986 B2 | 1/2012 | Puchhammer et al. |
| 8,257,446 B2 | 9/2012 | Puchhammer |
| 8,337,568 B2 | 12/2012 | Macduff |
| 8,343,234 B2 | 1/2013 | Puchhammer |
| 8,460,394 B2 | 6/2013 | Lee et al. |
| 8,491,666 B2 | 7/2013 | Schulz |
| 8,579,991 B2 | 11/2013 | Puchhammer |
| 8,662,552 B2 | 3/2014 | Torres-Jara |
| 8,663,339 B2 | 3/2014 | Inschlag et al. |
| 8,739,315 B2 | 6/2014 | Baacke |
| 8,747,486 B2 | 6/2014 | Kawasaki et al. |
| 8,795,387 B1 | 8/2014 | Razink |
| 8,803,844 B1 | 8/2014 | Green et al. |
| 8,808,397 B2 | 8/2014 | Gow |
| 8,900,327 B2 | 12/2014 | Bertels et al. |
| 8,915,528 B2 | 12/2014 | Haslinger |
| 8,920,519 B2 | 12/2014 | Johannes et al. |
| 8,951,303 B2 | 2/2015 | Dehoff et al. |
| 8,979,943 B2 | 3/2015 | Evans et al. |
| 8,984,736 B2 | 3/2015 | Radocy |
| 8,986,395 B2 | 3/2015 | McLeary |
| 8,999,003 B2 | 4/2015 | Wenstrand et al. |
| 9,016,744 B2 | 4/2015 | Starkey |
| 9,017,422 B2 | 4/2015 | Locker |
| 9,039,057 B2 | 5/2015 | Schvalb et al. |
| 9,071,170 B2 | 6/2015 | Baba et al. |
| 9,072,614 B2 | 7/2015 | Starkey et al. |
| 9,072,616 B2 | 7/2015 | Schulz |
| 9,101,499 B2 | 8/2015 | Haggas |
| 9,114,028 B2 | 8/2015 | Langenfeld et al. |
| 9,320,621 B2 | 4/2016 | Iversen et al. |
| 9,333,096 B2 | 5/2016 | Perez de Alderete et al. |
| 9,364,364 B2 | 6/2016 | Williams |
| 9,370,430 B2 | 6/2016 | Macduff |
| 9,375,319 B2 | 6/2016 | Macduff |
| 9,375,325 B2 | 6/2016 | Garrec et al. |
| 9,381,099 B2 | 7/2016 | Perry et al. |
| 9,387,095 B2 | 7/2016 | McLeary et al. |
| 9,402,749 B2 | 8/2016 | Gill et al. |
| 9,435,400 B2 | 9/2016 | Cheung et al. |
| 9,456,909 B2 | 10/2016 | Johnson et al. |
| 9,463,085 B1 | 10/2016 | Theobald |
| 9,468,540 B2 | 10/2016 | Nagatsuka et al. |
| 9,474,630 B2 | 10/2016 | Veatch |
| 9,474,631 B2 | 10/2016 | Veatch |
| 9,510,958 B2 | 12/2016 | Mori |
| 9,579,218 B2 | 2/2017 | Lipsey et al. |
| 9,579,219 B2 | 2/2017 | Amend, Jr. et al. |
| 9,585,771 B2 | 3/2017 | Baba et al. |
| 9,592,134 B2 | 3/2017 | Varley |
| 9,629,731 B2 | 4/2017 | Thompson, Jr. et al. |
| 9,636,270 B2 | 5/2017 | Miyazawa |
| 9,707,103 B2 | 7/2017 | Thompson, Jr. et al. |
| 9,730,813 B2 | 8/2017 | Evans et al. |
| 9,737,418 B2 | 8/2017 | Veatch |
| 9,744,055 B2 | 8/2017 | Engeberg et al. |
| 9,814,604 B2 | 11/2017 | Jury |
| 9,861,499 B2 | 1/2018 | Sensinger |
| 9,861,500 B2 | 1/2018 | Puchhammer |
| 9,877,848 B2 | 1/2018 | Ikebe |
| 9,889,059 B2 | 2/2018 | Arakawa |
| 9,913,737 B2 | 3/2018 | Hunter |
| 9,931,229 B2 | 4/2018 | Veatch |
| 9,974,667 B1 | 5/2018 | Cazenave |
| 9,999,522 B2 | 6/2018 | Gill |
| 10,004,611 B2 | 6/2018 | Iversen et al. |
| 10,004,612 B2 | 6/2018 | Iversen et al. |
| 10,022,248 B2 | 7/2018 | Thompson, Jr. et al. |
| 10,028,880 B2 | 7/2018 | Arata et al. |
| 10,034,780 B2 | 7/2018 | Lipsey et al. |

(56) References Cited

U.S. PATENT DOCUMENTS

| | | | |
|---|---|---|---|
| 10,045,865 B2 | 8/2018 | Veatch | |
| 10,045,866 B2 | 8/2018 | Armbruster | |
| 10,052,216 B2 | 8/2018 | Moyer et al. | |
| 10,076,425 B2 | 9/2018 | Farina et al. | |
| 10,092,423 B2 | 10/2018 | Goldfarb et al. | |
| D884,176 S | 5/2020 | Jury et al. | |
| 10,973,660 B2 | 4/2021 | Gill et al. | |
| 11,547,581 B2 | 1/2023 | Byrne et al. | |
| 11,786,381 B2 | 10/2023 | Gill et al. | |
| 11,931,270 B2 | 3/2024 | Rivera et al. | |
| 2002/0135241 A1 | 9/2002 | Kobayashi et al. | |
| 2003/0036805 A1 | 2/2003 | Senior | |
| 2004/0054423 A1 | 3/2004 | Martin | |
| 2004/0103740 A1 | 6/2004 | Townsend et al. | |
| 2005/0021154 A1 | 1/2005 | Brimalm | |
| 2005/0021155 A1 | 1/2005 | Brimalm | |
| 2005/0102037 A1 | 5/2005 | Matsuda | |
| 2005/0192677 A1 | 9/2005 | Ragnarsdottir et al. | |
| 2006/0158146 A1 | 7/2006 | Tadano | |
| 2006/0167564 A1 | 7/2006 | Flaherty et al. | |
| 2006/0212129 A1 | 9/2006 | Lake et al. | |
| 2007/0102228 A1 | 5/2007 | Shiina et al. | |
| 2007/0137351 A1 | 6/2007 | Schwendemann | |
| 2007/0276303 A1 | 11/2007 | Jenner, Jr. | |
| 2008/0097269 A1 | 4/2008 | Weinberg et al. | |
| 2008/0146981 A1 | 6/2008 | Greenwald et al. | |
| 2008/0262634 A1 | 10/2008 | Puchhammer | |
| 2009/0145254 A1 | 6/2009 | Hirabayashi et al. | |
| 2010/0016990 A1 | 1/2010 | Kurtz | |
| 2010/0036507 A1 | 2/2010 | Gow | |
| 2010/0116078 A1 | 5/2010 | Kim | |
| 2010/0274365 A1 | 10/2010 | Evans et al. | |
| 2011/0048098 A1 | 3/2011 | Rollins et al. | |
| 2011/0278061 A1 | 11/2011 | Farnan | |
| 2012/0221122 A1 | 8/2012 | Gill et al. | |
| 2012/0303136 A1 | 11/2012 | Macduff | |
| 2012/0330432 A1 | 12/2012 | Fong | |
| 2013/0030550 A1 | 1/2013 | Jopek et al. | |
| 2013/0076699 A1 | 3/2013 | Spencer | |
| 2013/0175816 A1 | 7/2013 | Kawasaki et al. | |
| 2013/0226315 A1 | 8/2013 | Varley | |
| 2013/0268090 A1 | 10/2013 | Goldfarb et al. | |
| 2013/0268094 A1 | 10/2013 | Van Wiemeersch | |
| 2013/0310949 A1 | 11/2013 | Goldfarb et al. | |
| 2013/0345828 A1 | 12/2013 | Starkey et al. | |
| 2014/0060236 A1 | 3/2014 | Watanabe | |
| 2014/0114439 A1 | 4/2014 | Iversen et al. | |
| 2014/0148918 A1 | 5/2014 | Pedersen et al. | |
| 2014/0148919 A1 | 5/2014 | Pedersen et al. | |
| 2014/0236314 A1 | 8/2014 | Van Wiemeersch | |
| 2014/0251056 A1 | 9/2014 | Preuss | |
| 2014/0277588 A1 | 9/2014 | Patt et al. | |
| 2014/0288665 A1 | 9/2014 | Gill | |
| 2015/0112448 A1 | 4/2015 | Scott et al. | |
| 2015/0183069 A1 | 7/2015 | Lee | |
| 2015/0190245 A1 | 7/2015 | McLeary et al. | |
| 2015/0216679 A1 | 8/2015 | Lipsey et al. | |
| 2015/0351935 A1 | 12/2015 | Donati et al. | |
| 2015/0360369 A1 | 12/2015 | Ishikawa et al. | |
| 2015/0374515 A1 | 12/2015 | Meijer et al. | |
| 2016/0089251 A1 | 3/2016 | Mandl et al. | |
| 2016/0166409 A1 | 6/2016 | Goldfarb et al. | |
| 2016/0235555 A1 | 8/2016 | Hunter | |
| 2016/0250044 A1 | 9/2016 | Iversen et al. | |
| 2016/0296345 A1 | 10/2016 | Deshpande et al. | |
| 2016/0367383 A1 | 12/2016 | Sensinger et al. | |
| 2017/0007424 A1 | 1/2017 | Gill | |
| 2017/0014245 A9 | 1/2017 | Hunter | |
| 2017/0168565 A1 | 6/2017 | Cohen et al. | |
| 2017/0340459 A1 | 11/2017 | Mandelbaum | |
| 2018/0036145 A1 | 2/2018 | Jury et al. | |
| 2018/0098862 A1 | 4/2018 | Kuiken et al. | |
| 2018/0116829 A1 | 5/2018 | Gaston et al. | |
| 2018/0133032 A1 | 5/2018 | Poirters | |
| 2018/0140441 A1 | 5/2018 | Poirters | |
| 2018/0168830 A1 | 6/2018 | Evans et al. | |
| 2018/0202538 A1 | 7/2018 | Wilson-Jones et al. | |
| 2018/0207005 A1 | 7/2018 | Chen et al. | |
| 2018/0221177 A1 | 8/2018 | Kaltenbach et al. | |
| 2018/0256365 A1 | 9/2018 | Bai | |
| 2018/0256366 A1 | 9/2018 | Bai | |
| 2018/0256367 A1 | 9/2018 | Bai | |
| 2018/0263791 A1 | 9/2018 | Bai | |
| 2018/0296368 A1 | 10/2018 | Gill | |
| 2018/0303633 A1 | 10/2018 | Yi | |
| 2019/0209345 A1 | 7/2019 | LaChappelle | |
| 2019/0368237 A1 | 12/2019 | Distefano et al. | |
| 2020/0047351 A1 | 2/2020 | Zappatore | |
| 2020/0306059 A1 | 10/2020 | Cornman et al. | |
| 2021/0145610 A1 | 5/2021 | Rivera et al. | |
| 2021/0251779 A1 | 8/2021 | Mark | |
| 2021/0307934 A1 | 10/2021 | Gill et al. | |
| 2021/0361446 A1 | 11/2021 | Griebling et al. | |
| 2022/0313456 A1 | 10/2022 | Acevedo et al. | |
| 2022/0339009 A1 | 10/2022 | Benning | |
| 2023/0033693 A1 | 2/2023 | Babin et al. | |
| 2023/0088565 A1 | 3/2023 | Benning | |
| 2024/0074878 A1 | 3/2024 | Gill et al. | |
| 2024/0245532 A1 | 7/2024 | Rivera et al. | |
| 2024/0299192 A1 | 9/2024 | Rivera et al. | |
| 2024/0299193 A1 | 9/2024 | Rivera et al. | |
| 2024/0390164 A1 | 11/2024 | Griebling et al. | |

FOREIGN PATENT DOCUMENTS

| | | | |
|---|---|---|---|
| CN | 204274727 | 4/2015 | |
| CN | 103830025 | 8/2015 | |
| CN | 103705323 | 3/2016 | |
| CN | 106994694 | 8/2017 | |
| CN | 108 272 537 | 7/2018 | |
| CN | 106491250 | 9/2018 | |
| CN | 109 620 487 | 4/2019 | |
| CN | 110 340 913 | 10/2019 | |
| CN | 112 873 252 | 6/2021 | |
| CN | 108 544 518 | 5/2024 | |
| DE | 309 367 | 11/1918 | |
| DE | 319 092 | 2/1920 | |
| DE | 323 970 | 8/1920 | |
| DE | 24 34 834 | 2/1976 | |
| DE | 26 07 499 | 9/1977 | |
| DE | 198 54 762 | 6/2000 | |
| DE | 101 05 814 | 9/2002 | |
| DE | 203 01 116 | 3/2003 | |
| DE | 698 16 848 | 4/2004 | |
| DE | 10 2012 009 699 | 11/2013 | |
| DE | 10 2017 005 761 | 2/2020 | |
| DE | 10 2017 005 762 | 2/2020 | |
| DE | 10 2017 005 764 | 2/2020 | |
| DE | 10 2017 005 765 | 2/2020 | |
| EP | 0 145 504 | 6/1985 | |
| EP | 0 484 173 | 5/1992 | |
| EP | 1 043 003 | 10/2000 | |
| EP | 1 557 547 | 1/2011 | |
| EP | 2 612 619 | 7/2013 | |
| EP | 2 616 017 | 7/2013 | |
| EP | 2 653 137 | 10/2013 | |
| EP | 2 664 302 | 11/2013 | |
| EP | 2 719 361 | 4/2014 | |
| EP | 2 114 315 | 5/2016 | |
| EP | 2 890 333 | 12/2016 | |
| EP | 2 978 389 | 5/2017 | |
| EP | 3 589 242 | 1/2020 | |
| EP | 3 996 885 | 8/2023 | |
| EP | 3 977 965 | 2/2024 | |
| GB | 239004 | * 9/1925 | ............ A61F 2/54 |
| GB | 326 970 | 3/1930 | |
| GB | 1 510 298 | 5/1978 | |
| GB | 1 585 256 | 2/1981 | |
| GB | D 3023680 | 4/2006 | |
| GB | 2 444 679 | 6/2008 | |
| GB | 2 521 748 | 7/2015 | |
| GB | 2521748 A | * 7/2015 | ............ B25J 15/00 |
| JP | 53-011456 | 2/1978 | |
| JP | 2002-310242 | 10/2002 | |

(56) References Cited

FOREIGN PATENT DOCUMENTS

| | | |
|---|---|---|
| JP | 2004-224280 | 8/2004 |
| JP | 2018-167375 | 11/2018 |
| WO | WO 95/024875 | 9/1995 |
| WO | WO 99/021517 | 5/1999 |
| WO | WO 00/069375 | 11/2000 |
| WO | WO 03/017878 | 3/2003 |
| WO | WO 03/017880 | 3/2003 |
| WO | WO 2006/069264 | 6/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044207 | 4/2008 |
| WO | WO 2008/098059 | 8/2008 |
| WO | WO 2008/098072 | 8/2008 |
| WO | WO 2010/018358 | 2/2010 |
| WO | WO 2010/050765 | 5/2010 |
| WO | WO 2010/051798 | 5/2010 |
| WO | WO 2011/001136 | 1/2011 |
| WO | WO 2011/022569 | 2/2011 |
| WO | WO 2011/036473 | 3/2011 |
| WO | WO 2011/107778 | 9/2011 |
| WO | WO 2013/038143 | 3/2013 |
| WO | WO 2013/185231 | 12/2013 |
| WO | WO 2014/016581 | 1/2014 |
| WO | WO 2014/027897 | 2/2014 |
| WO | WO 2014/177272 | 11/2014 |
| WO | WO 2015/128604 | 9/2015 |
| WO | WO 2017/061879 | 4/2017 |
| WO | WO 2017/084637 | 5/2017 |
| WO | WO 2017/199127 | 11/2017 |
| WO | WO 2017/212128 | 12/2017 |
| WO | WO 2018/006722 | 1/2018 |
| WO | WO 2018/054945 | 3/2018 |
| WO | WO 2018/056799 | 3/2018 |
| WO | WO 2018/096188 | 5/2018 |
| WO | WO 2018/121983 | 7/2018 |
| WO | WO 2018/130428 | 7/2018 |
| WO | WO 2018/132711 | 7/2018 |
| WO | WO 2018/158554 | 9/2018 |
| WO | WO 2018/178420 | 10/2018 |
| WO | WO 2018/180782 | 10/2018 |
| WO | WO 2018/218129 | 11/2018 |
| WO | WO 2020/019992 | 1/2020 |
| WO | WO 2020/199240 | 10/2020 |
| WO | WO 2020/208557 | 10/2020 |
| WO | WO 2020/234777 | 11/2020 |
| WO | WO 2021/053557 | 3/2021 |
| WO | WO 2021/095014 | 5/2021 |
| WO | WO 2021/244708 | 12/2021 |
| WO | WO 2023/080796 | 5/2023 |

OTHER PUBLICATIONS

Plaintiff Vincent Systems GmbH's Supplemental Disclosure of Asserted Claims and Infringement Contentions dated Jul. 16, 2020, in 38 pages, in the lawsuit of *Vincent Systems GmbH v. Össur hf. and Össur Americas, Inc.* (collectively "Össur"), in the United States District Court, Central District of California, Case No. 8:19-VC-02157 JLS (DFMx). This reference includes information regarding Össur's products that were on sale prior to the Apr. 10, 2019 priority date of the present application. Applicant requests that the Examiner consider the information describing details of Össur's products to have been described in a printed publication, or in public use, on sale, or otherwise available to the public, prior to the Apr. 10, 2019 priority date of the present application.
The Edinburgh Modular Arm System (EMAS), as described in the Edinburgh Modular Arm System (EMAS) Explanation of Relevance in 3 pages. Applicant requests that the Examiner consider this reference to have been described in a printed publication, or in public use, on sale, or otherwise available to the public, prior to the Apr. 10, 2019 priority date of the present application.
9 Worm Gear Pair, KHK Technical Information, Oct. 21, 2008, pp. 291-299.
Adee, Sally, "A 'Manhattan Project' for the Next Generation of Bionic Arms", IEEE Spectrum, https://spectrum.ieee.org/a-manhattan-project-for-the-next-generation-of-bionic-arms#toggle-gdpr, Mar. 22, 2008, pp. 3.
AMA, Excerpts from American Medical Association, Guides to the Evaluation of Permanent Impairment (5th ed. 2000), pp. 432-453.
Baek et al., "Design and Control of a Robotic Finger for Prosthetic Hands", Proceedings of the 1999 IEEE International Conference on Intelligent Robots and Systems, pp. 113-117.
Belter et al., "Mechanical Design and Performance Specifications of Anthropomorphic Prosthetic Hands: A Review", JRRD, Nov. 5, 2013, vol. 50, No. 5, pp. 599-617.
Bretthauer et al., "A New Adaptive Hand Prosthesis", Handchirurgie Mikrochirurgie Plastische Chirurgie, Feb. 2008, pp. 40-45.
Butterfarß et al., "DLR-Hand II: Next Generation of a Dextrous Robot Hand", IEEE International Conference on Robotics and Automation, Seoul, Korea, May 21-26, 2001, vol. 1, pp. 109-114.
Connolly, "Prosthetic Hands from Touch Bionics", Industrial Robot, Emerald Group Publishing Limited, Jun. 2008, vol. 35, No. 4, pp. 290-293.
Cotton et al., "Control Strategies for a Multiple Degree of Freedom Prosthetic Hand", Measurement + Control, Feb. 2007, vol. 40, No. 1, pp. 24-27.
Dimery, Rob, "1993: First Bionic Arm", Guinness World Records, https://www.guinnessworldrecords.com/news/60at60/2015/8/1993-first-bionic-arm-392887, Aug. 18, 2015, pp. 2.
"DuPont Engineering Design—The Review of DuPont Engineering Polymers in Action", <http://www.engpolymer.co.kr/x_data/magazine/engdesign07_2e.pdf>, Feb. 2007, pp. 16.
Edsinger-Gonzales, Aaron, "Design of a Compliant and Force Sensing Hand for a Humanoid Robot", 2005, pp. 5.
"EMAS: The First Bionic Arm", National Museums Scotland, https://web.archive.org/web/20200805045443/https://www.nms.ac.uk/explore-our-collections/stories/science-and-technology/made-in-scotland-changing-the-world/scottish-science-innovations/emas-bionic-arm/, archived Aug. 5, 2020, pp. 8.
Fildes, Jonathan, "Bionic Hand Wins Top Tech Prize", BBC News, Jun. 9, 2008, http://news.bbc.co.uk/2/hi/science/nature/7443866.stm, pp. 3.
Gaiser et al., "A New Anthropomorphic Robotic Hand", 2008 8th IEEE-RAS International Conference on Humanoid Robots, Dec. 1-3, 2008, Daejeon, Korea, pp. 418-422.
Goggins, Sophie, "EMAS—An Award Winning Bionic Arm", National Museums Scotland, https://blog.nms.ac.uk/2017/11/29/emas-an-award-winning-bionic-arm/, Nov. 29, 2017, pp. 6.
Gow, David, "The Development of the Edinburgh Modular Arm System", Institute of Biomedical Engineering, University of New Brunswick, MEC '99 "Narrowing the Gap", pp. 64-66, 1999.
Grant, C. "Touch Bionics has i-LIMB Bionic Arm to go with your Bionic Hand", Engadget, https://www.engadget.com/2008-01-05-touch-bionics-has-i-limb-bionic-arm-to-go-with-your-bionic-hand.html, Jan. 6, 2008, p. 1.
Greenemeier, Larry, "Bionic Hand Recognized as Top Invention", Scientific American, https://blogs.scientificamerican.com/news-blog/bionic-hand-recognized-as-top-inven-2008-11-06, Nov. 6, 2008, pp. 3.
"i-Limb™ Hand", Touch Bionics, User Manual, Revision 1.5, 2007, pp. 12.
"iLimb Bionic Hand Now Ready for Market", Technovelgy.com, www.technovelgy.com/ct/Science-Fiction-News.asp?NewsNum=1125, as printed Jul. 6, 2020 in 3 pages.
Kargov et al., "Applications of a Fluidic Artificial Hand in the Field of Rehabilitation", Rehabilitation Robotics, Ch. 15, Aug. 2007, pp. 261-286.
Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.

(56) References Cited

OTHER PUBLICATIONS

Kargov et al., "Modularly Designed Lightweight Anthropomorphic Robot Hand", 2006 IEEE International Conference on Multisensor Fusion and Integration for Intelligent Systems, Sep. 3-6, 2006, Heidelberg, Germany, pp. 155-159.
Kawasaki et al., "Design and Control of Five-Fingered Haptic Interface Opposite to Human Hand", IEEE Transactions on Robotics, Oct. 2007, vol. 23, No. 5., pp. 909-918.
"Living with a Dead Man's Hand", BBC News, http://news.bbc.co.uk/2/hi/health/980069.stm, Oct. 22, 2000, pp. 4.
Lotti et al., "UBH 3: A Biologically Inspired Robotic Hand", Jan. 2004, pp. 7.
MEC '05: Integrating Prosthetics and Medicine, University of New Brunswick's MyoElectric Controls/Powered Prosthetics Symposium, Aug. 17-19, 2005, Fredericton NB Canada, pp. 260.
Miller et al., "Control of a Six Degree of Freedom Prosthetic Arm After Targeted Muscle Reinnervation Surgery", Archives of Physical Medicine and Rehabilitation, Nov. 2008, vol. 89, pp. 2057-2065.
"Motor Technology—Girard Gearboxes Low Backlash Principle Explained", Motor Technology, https://www.motec.co.uk/tip-gearbox_principle.htm as printed May 23, 2012 in 3 pages.
Pilgrim, Michael, "Meet the Man Who Was Given Britain's First Bionic Hand on the NHS—and is now Learning to Fly", Daily Mail, https://www.dailymail.co.uk/health/article-1038857/Meet-man-given-Britains-bionic-hand-NHS--learning-fly.html, Jul. 26, 2008, pp. 7.
Poppe, Zytel HTN Provides a Helping Hand, DuPont Engineering Design 8 (2007), pp. 3.
"ProDigits The Partial Hand Solution", Touch Bionics, Next Generation Bionic Technology: Transforming the everyday lives of extraordinary people, 2007, pp. 4.
Puig et al., "A Methodology for the Design of Robotic Hands with Multiple Fingers", International Journal of Advanced Robotic Systems, 2008, vol. 5, No. 2, pp. 177-184.
Roberts, Lizzie, "Bionic Hand Among Top Inventions of 2008", The Telegraph, https://www.telegraph.co.uk/news/health/3391089/Bionic-hand-among-top-inventions-of-2008.html, Nov. 6, 2008, pp. 2.
Ryew et al., "Robotic Finger Mechanism with New Anthropomorphic Metacarpal Joint", 26th Annual Conference of the IEEE Industrial Electronics Society, 2000. IECON 2000, vol. 1, pp. 416-421.
Sensinger et al., "Cycloid vs. Harmonic Drives for use in High Ratio, Single Stage Robotic Transmissions", 2012 IEEE Conference on Robotics and Automation (ICRA), Saint Paul, MN, USA, May 14-18, 2012, pp. 4130-4135.
Shigley's Mechanical Engineering Design Eighth Edition, ISBN 0-390-76487-6 (2008), pp. 1059.
Shigley's Mechanical Engineering Design Seventh Edition, ISBN 0-07-252036-1 (2004), pp. 1064.
Stix, Gary, "Phantom Touch: Imbuing a Prosthesis with Manual Dexterity", Scientific American, Oct. 1998, pp. 41 & 44.
"The i-LIMB Hand", Touch Bionics, Fitting Guide, 2005, pp. 22.
"The i-LIMB Hand", Touch Bionics, Next Generation Bionic Technology: Transforming the everyday lives of extraordinary people, 2007, pp. 8.
Topolsky, J., "Touch Bionics i-LIMB Bionic Hand", Engadget, https://www.engadget.com/2007-07-17-touch-bionics-i-limb-bionic-hand.html, Jul. 17, 2007, p. 1.
Touch Bionics PowerPoint presentation in 12 pages, Oct. 17, 2006, The i-LIMB™ System. (Applicant requests that the Examiner consider this reference as qualifying as prior art as of the date indicated, but Applicant does not admit its status as prior art by submitting it here and reserves the right to challenge the reference's prior art status at a later date).
Touch Bionics PowerPoint presentation in 32 p. 2005, The i-LIMB™ System. (Applicant requests that the Examiner consider this reference as qualifying as prior art as of the date indicated, but Applicant does not admit its status as prior art by submitting it here and reserves the right to challenge the reference's prior art status at a later date).
Weir et al., "A Myoelectrically Controlled Prosthetic Hand for Transmetacarpal Amputations", JPO Journal of Prosthetics and Orthotics, Jun. 2001, vol. 13, No. 2, pp. 26-31.
Weir et al., "The Design and Development of a Synergetic Partial Hand Prosthesis with Powered Fingers", RESNA '89, Proceedings of the 12th Annual Conference, Technology for the Next Decade, Jun. 25-30, 1989, pp. 473-474.
"World's First Bionic Arm for Scot", BBC News, http://news.bbc.co.uk/2/hi/health/154545.stm, Aug. 25, 1998, pp. 3.
"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.
Amended Complaint for Patent Infringement in 166 pages filed by Vincent Systems GmbH, dated Apr. 15, 2020, in the lawsuit of *Vincent Systems GmbH v. Össur hf. and Össur Americas, Inc.* (collectively "Össur"), in the United States District Court, Central District of California, Case No. 8:19-VC-02157 JLS (DFMx), including Exhibits A-J. The Amended Complaint and the accompanying Exhibits include information regarding Össur's products that were on sale prior to the Nov. 15, 2019 priority date of the present application and were accused of infringement. Applicant requests that the Examiner consider the information describing details of Össur's products to have been described in a printed publication, or in public use, on sale, or otherwise available to the public, prior to the Nov. 15, 2019 priority date of the present application.
Complaint in 36 pages and English translation in 35 pages of the Complaint filed at the Regional Court Mannheim by the law firm Bardehle Pagenberg on behalf of Vincent Systems GmbH, dated Nov. 24, 2016, in the lawsuit of *Vincent Systems GmbH v. Touch Bionics Limited and Touch Bionics GmbH* (collectively "Touch"), and accompanying Exhibits K1-K23 (each listed separately herewith). The Complaint and the accompanying Exhibits include information regarding Touch's products that were on sale prior to the Nov. 15, 2019 priority date of the present application and were accused of infringement. Applicant requests that the Examiner consider the information describing details of Touch's products to have been described in a printed publication, or in public use, on sale, or otherwise available to the public, prior to the Nov. 15, 2019 priority date of the present application.
Exhibit K1—Companies House as printed Jul. 27, 2016 in 1 page.
Exhibit K3—Touch Bionics Limited, Directors' Report and Financial Statements, Dec. 31, 2015 in 64 pages.
Exhibit K4—EP 2 364 129 as published Jun. 19, 2013 in 12 pages.
Exhibit K6—Notice of Change of Name by Resolution as filed Jun. 12, 2014 in 4 pages.
Exhibit K8—WO 2007/063266 as published Jun. 7, 2007 in 30 pages.
Exhibit K19—Touch Bionics, i-digits quantum, dated Nov. 20, 2016 in 3 pages.
Exhibit K20—Touch Bionics, Document Library, dated Nov. 20, 2016 in 8 pages.
Exhibit K21—Touch Bionics, i-digits quantum, 2016 in 1 page.
Exhibit K22—Whols—Touch Bionics, printed Nov. 20, 2016 in 2 pages.
I-Limb and Pro-Digits products, on sale or in public use in the United States by May 31, 2007, including a photograph, engineering drawings and assembly instructions, as described in the i-Limb and Pro-Digits Explanation of Relevance in 19 pages.
I-Limb Shoulder, on sale in the United States at least as early as 2005, as described in the i-Limb Shoulder Explanation of Relevance in 2 pages.
Plaintiff Vincent Systems GmbH's Supplemental Disclosure of Asserted Claims and Infringement Contentions dated Jul. 16, 2020, in 38 pages, in the lawsuit of *Vincent Systems GmbH v. Össur hf. and Össur Americas, Inc.* (collectively "Össur"), in the United States District Court, Central District of California, Case No. 8:19-VC-02157 Jls (DFMx). This reference includes information regarding Össur's products that were on sale prior to the Nov. 15, 2019 priority date of the present application. Applicant requests that the Examiner consider the information describing details of Össur's products to have been described in a printed publication, or in public

(56) References Cited

OTHER PUBLICATIONS use, on sale, or otherwise available to the public, prior to the Nov. 15, 2019 priority date of the present application.
The Edinburgh Modular Arm System (EMAS), as described in the Edinburgh Modular Arm System (EMAS) Explanation of Relevance in 3 pages. Applicant requests that the Examiner consider this reference to have been described in a printed publication, or in public use, on sale, or otherwise available to the public, prior to the Nov. 15, 2019 priority date of the present application.
International Search Report and Written Opinion in Application No. PCT/IB2020/053373, mailed Jun. 15, 2020.
Complaint in 36 pages and English translation in 35 pages of the Complaint filed at the Regional Court Mannheim by the law firm Bardehle Pagenberg on behalf of Vincent Systems GmbH, dated Nov. 24, 2016, in the lawsuit of *Vincent Systems GmbH* v. *Touch Bionics Limited and Touch Bionics GmbH* (collectively "Touch"), and accompanying Exhibits K1-K23 (each listed separately herewith). The Complaint and the accompanying Exhibits include information regarding Touch's products that were on sale prior to the Apr. 10, 2019 priority date of the present application and were accused of infringement. Applicant requests that the Examiner consider the information describing details of Touch's products to have been described in a printed publication, or in public use, on sale, or otherwise available to the public, prior to the Apr. 10, 2019 priority date of the present application.
Schulz et al., "Die Entwicklung Einer Multifunktionalen Kosmetischen Handprothese", Prothetik, Orthopädie-Technik, Aug. 2006, pp. 627-628 & 630-632.
The Weir Thesis ("Weir Thesis") is entitled "An Externally-Powered, Myo-Electrically Controlled Synergetic Prosthetic Hand for the Partial-Hand Amputee", published Aug. 1989, pp. 365 (pp. 11 & 52 unavailable).
Ward, Derek Kempton, "Design of a Two Degree of Freedom Robotic Finger", Thesis, University of Canterbury, Christchurch, NZ, https://ir.canterbury.ac.nz/items/62af5846-6c15-49f3-8772-3f23b9823cf4, Sep. 1996, in 155 pages (pp. 93-94 unavailable).
"Axon-Bus Prosthetic System" User Manual, Ottobock, Apr. 15, 2021, 308 pages (English translation on pp. 24-46).
"Functional Devices—Split Hooks and Spare Parts", Steeper, Wayback Machine, Mar. 20, 2023, 3 pages. URL: https://www.steepergroup.com/SteeperGroup/media/SteeperGroupMedia/Prosthetics/Upper%20Limb%20Prosthetics/Split-Hook-Catalogue-Pages_1.pdf.
"Hero Flex", Open Bionics, Wayback Machine, Dec. 8, 2023, 13 pages. URL: https://openbionics.com/heroflex/.
"MyoHand VariPlus Speed", Ottobock, Wayback Machine, Sep. 30, 2023, 6 pages. URL: https://www.ottobock.com/en-us/product/8E38~59.
"ProPlus MC ETD", Fillauer, Wayback Machine, Sep. 24, 2023, 5 pages. URL: https://fillauer.com/products/proplus-mc-etd/.
"ProPlus MC ETD2", Fillauer, Wayback Machine, Sep. 28, 2023, 5 pages. URL: https://fillauer.com/products/proplus-mc-etd2/.
"Quick Disconnect Wrist", Steeper, Wayback Machine, Sep. 26, 2023, 6 pages. URL: https://www.steepergroup.com/prosthetics/upper-limb-prosthetics/wrists/quick-disconnect-wrist/.
Sears, "Evaluation and Development of a New Hook-Type Terminal Device", Department of Bioengineering, The University of Utah, Jun. 1983, 151 pages.
"System Electric Hand Digital Twin", Ottobock, Wayback Machine, Mar. 29, 2023, 4 pages. URL: https://www.ottobock.com/en-us/product/8E38~57.

\* cited by examiner

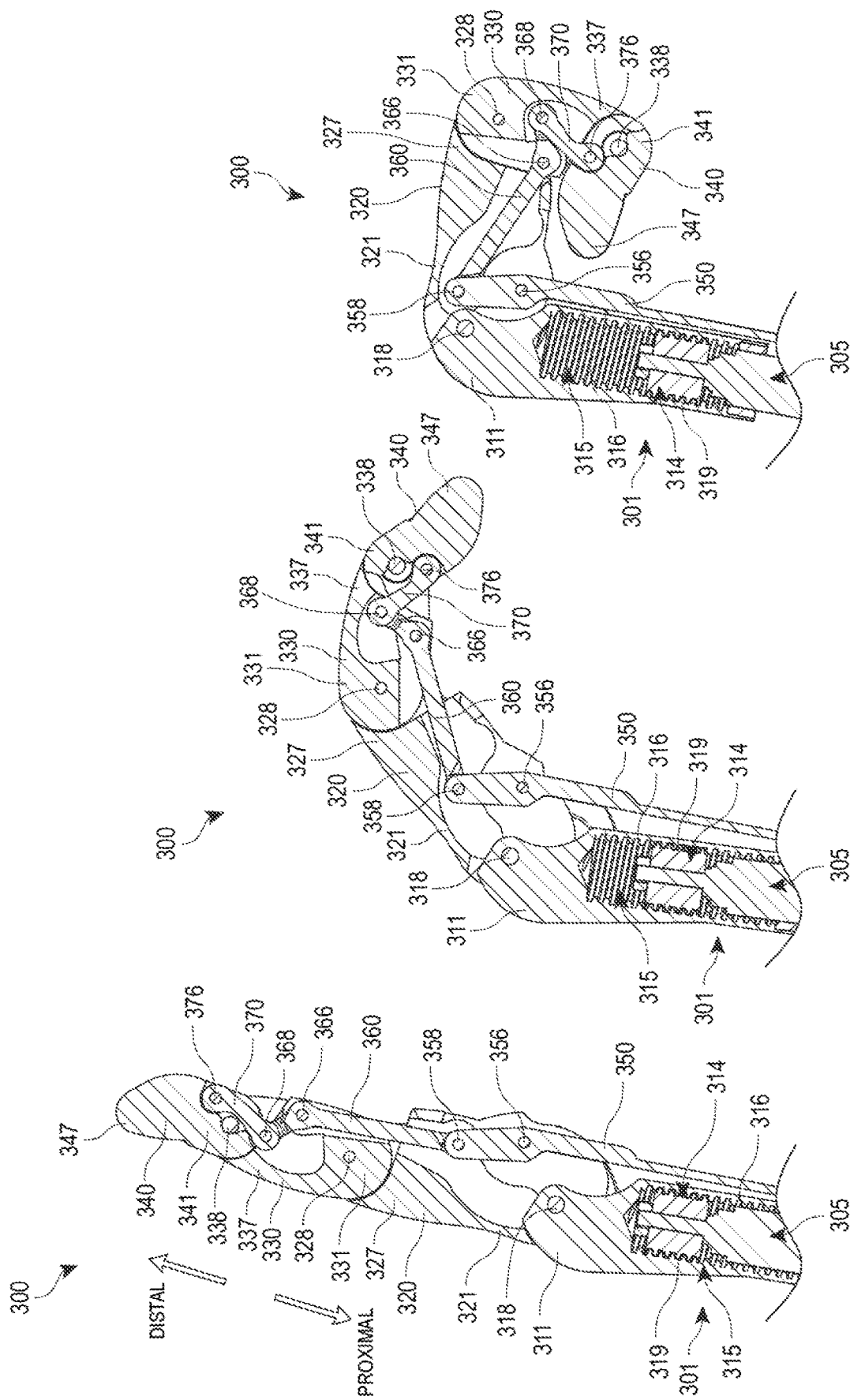

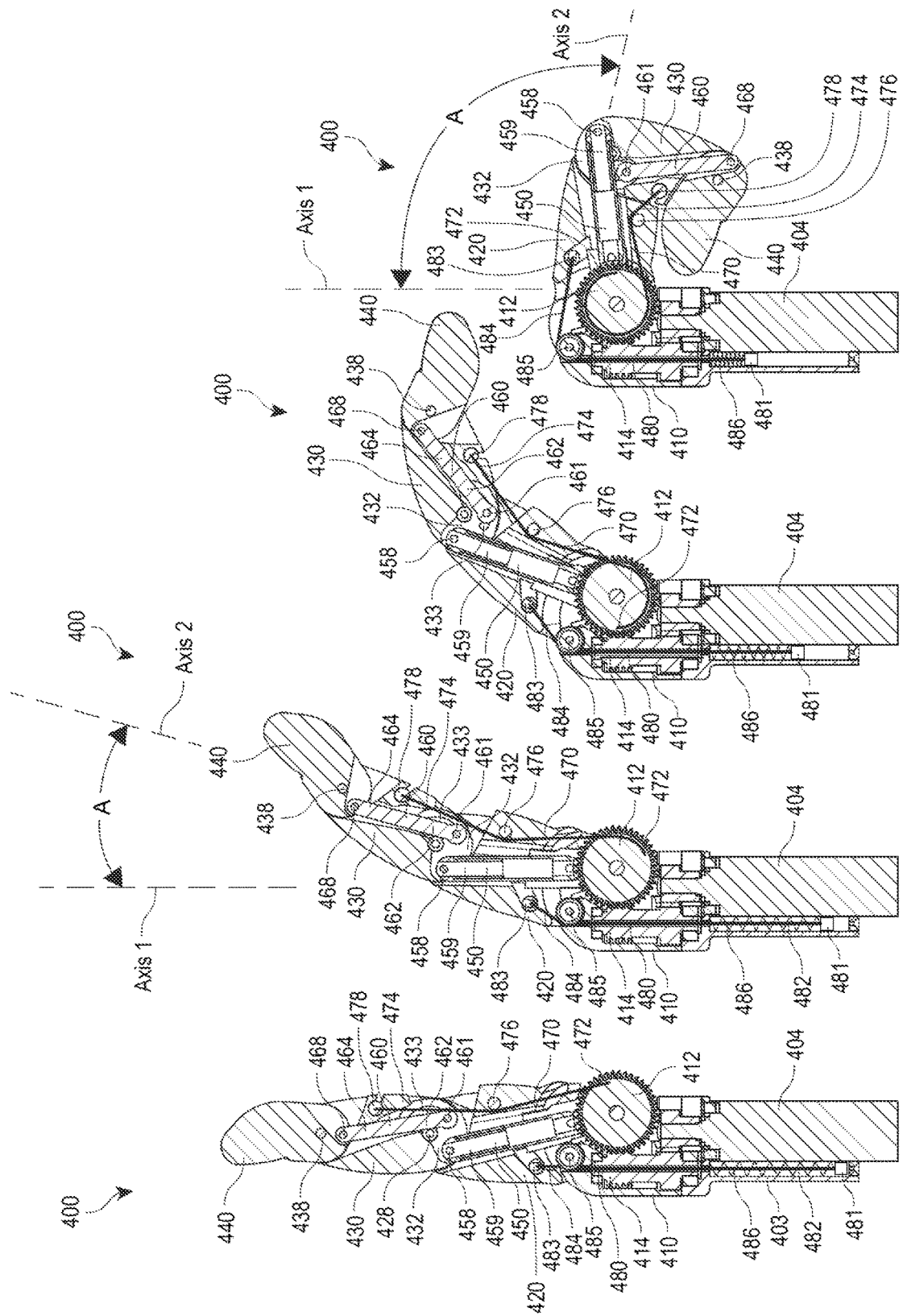

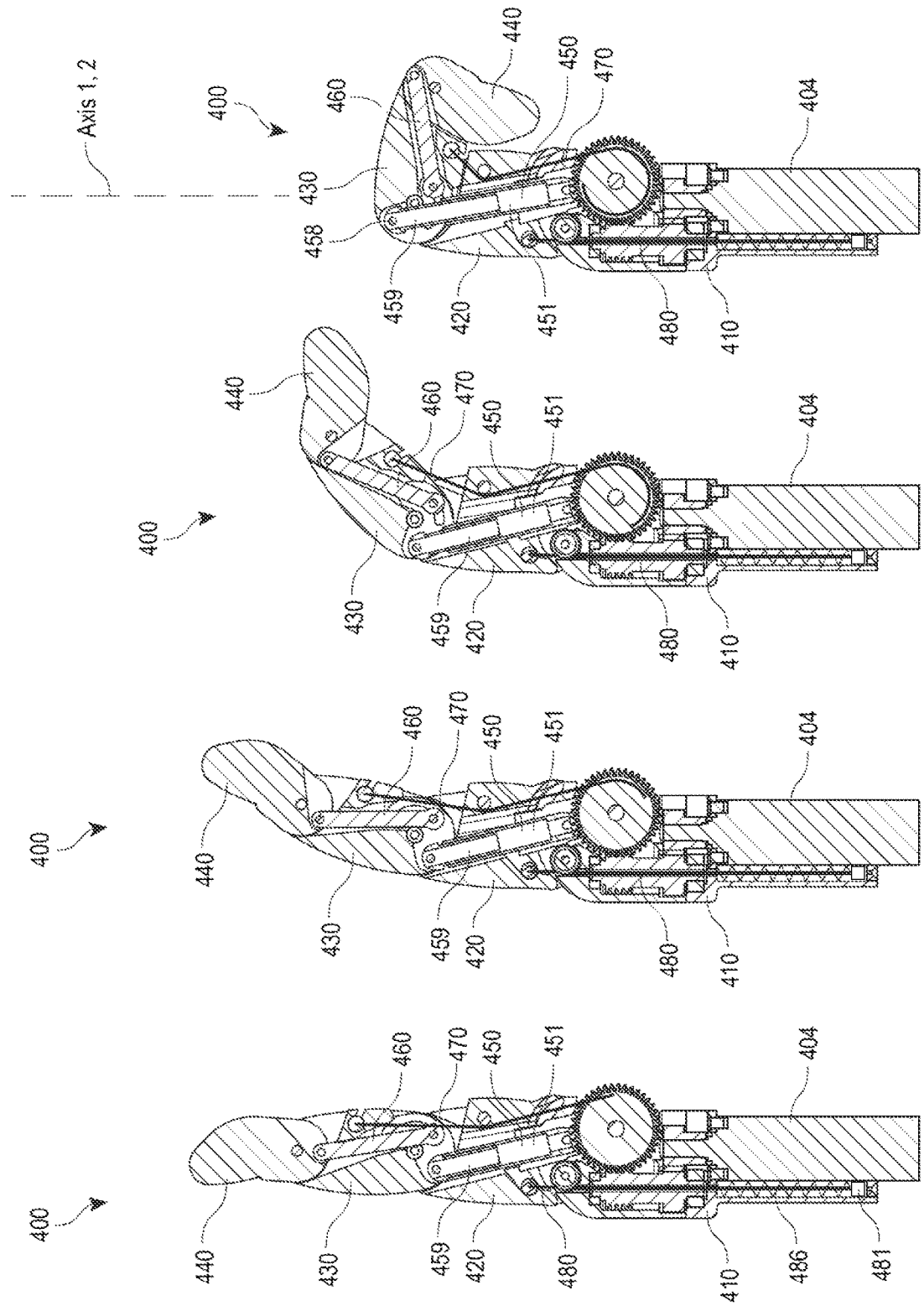

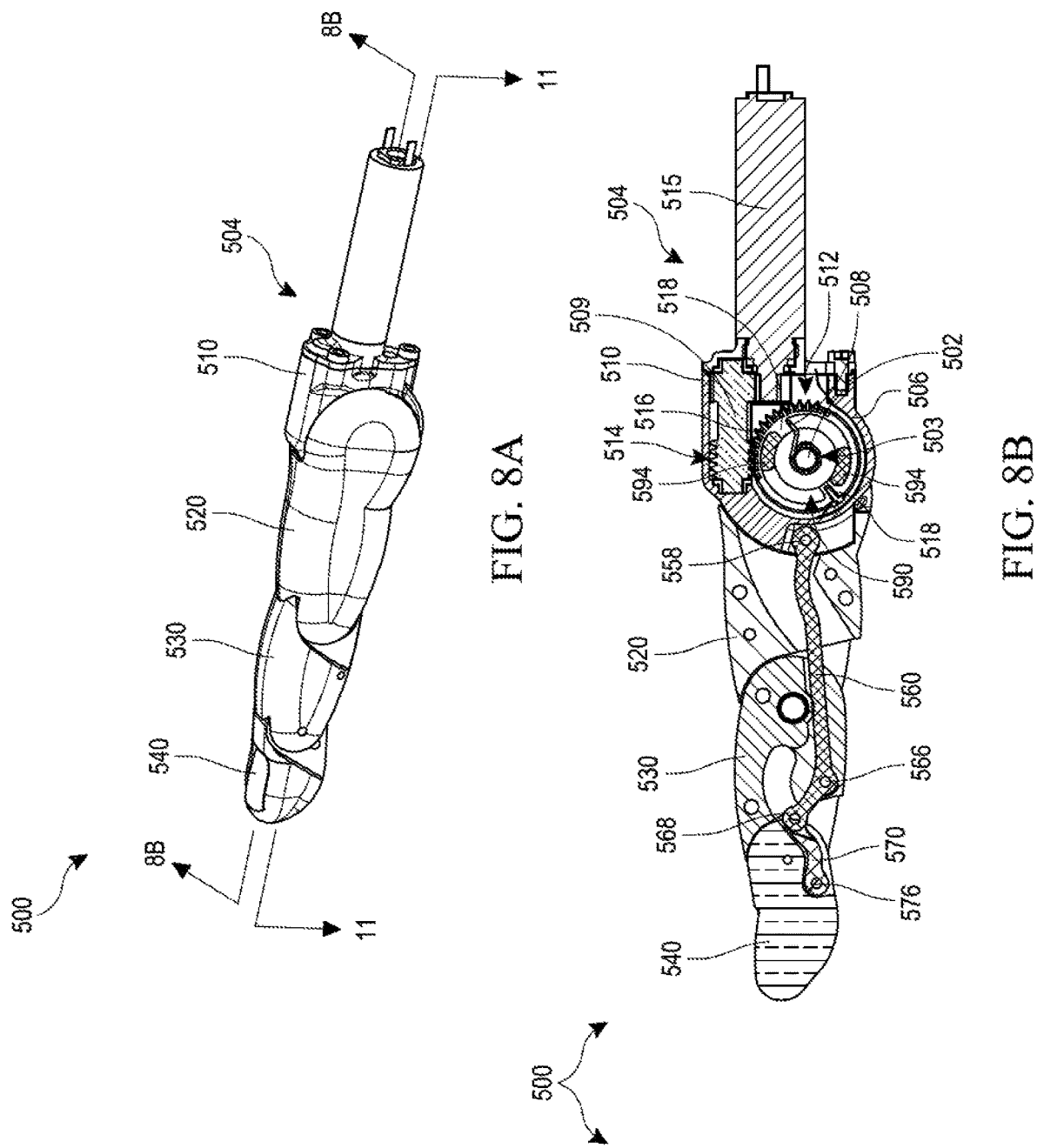

PROSTHETIC DIGIT WITH ARTICULATING LINKS

INCORPORATION BY REFERENCE TO ANY PRIORITY APPLICATIONS

Any and all applications for which a foreign or domestic priority claims is identified in the Application Data Sheet as filed with the present application are hereby incorporated by reference under 37 CFR. 1.37.

BACKGROUND

Field

Features for prosthetics are described, in particular prosthetic digits.

Description of the Related Art

Prosthetic digits are useful for amputees missing natural fingers. Existing solutions to prosthetic digits do not sufficiently mimic natural fingers and so functionality is not fully restored. Improvements to prosthetic digits are therefore desirable.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for prosthetic digits.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

Features for prosthetic digits are described. The digits mimic natural fingers by having three articulating segments, including a proximal, middle and distal segment. The segments are articulated by an actuator and mechanical links configured to cause rotation of the segments. The digit may have multiple degrees of freedom. A single actuator may be used for a single digit. A tendon may be used in some versions. The rotated digit may provide articulation that mimics a natural finger and thus fully surrounds a variety of shapes and sizes of objects to provide and restore enhanced gripping functionality to amputees. The digit provides space, weight and power savings due to the need for only a single actuator. A spring-biased worm wheel transmission provides a manual mode for rotation of the digit and prevents damage due to rotation induced by external forces acting on the digit.

In one aspect, a prosthetic digit is described. The prosthetic digit comprises a mount, a proximal segment, a middle segment, a distal segment, a proximal link, a distal link, and an actuator. The mount is configured to attach to a hand. The proximal segment is rotatably attached to the mount at a first pivot, and the middle segment is rotatably attached to the proximal and distal segments. The proximal link is rotatably attached to the mount and rotatably attached to the middle segment at a second pivot. The distal link is rotatably attached to the proximal link and rotatably attached to the distal segment at a third pivot. The actuator is coupled with the mount and the proximal segment, and the actuator is configured to cause the proximal segment to rotate about the first pivot, where rotation of the proximal segment about the first pivot causes the middle and distal segments to rotate.

In another aspect, a prosthetic digit is described. The prosthetic digit comprises a mount, a plurality of articulating segments comprising a proximal articulating segment, and an actuator. The mount is configured to attach to a hand. The proximal segment is rotatably attached to the mount at a first pivot and is rotatably attached to the actuator at a first joint. The first joint is located offset from the first pivot, such that linear actuation output by the actuator imposes a force at the first joint to cause the proximal segment to rotate about the first pivot.

In another aspect, a prosthetic hand is described that includes the prosthetic digit.

In another aspect, a prosthetic digit is described that comprises a mount, a proximal segment, a middle segment, a distal segment, a proximal expandable link, and an actuator. The mount is configured to attach to a hand. The proximal segment is rotatably attached to the mount, and the middle segment is rotatably attached to the proximal and distal segments. The proximal expandable link is rotatably coupled with the mount and configured to expand linearly such that the middle and distal segments can rotate independently of rotation of the proximal segment. The actuator is in mechanical communication with the middle and distal segments and configured to cause the middle and distal segments to rotate. In some embodiments, the actuator is in mechanical communication with the proximal segment via a tendon.

In some embodiments, the prosthetic digit further comprises a distal link rotatably coupled with the proximal expandable link and with the distal segment.

In some embodiments, the proximal expandable link comprises a proximal portion, a distal portion, and a spring, where the proximal portion is in mechanical communication with the distal portion via the spring.

In another aspect, a prosthetic digit is described that comprises a mount, a plurality of articulating segments, and an actuator. The mount is configured to attach to a hand. The plurality of articulating segments comprise a proximal articulating segment. The proximal segment is rotatably attached to the mount at a first pivot, the proximal segment is rotatably attached to the actuator at a first joint, and the first joint is located offset from the first pivot, such that linear actuation output by the actuator imposes a force at the first joint to cause the proximal segment to rotate about the first pivot.

BRIEF DESCRIPTION OF THE DRAWINGS

FIGS. 3F-3H are sequential views of the prosthetic digit of FIGS. 3A-3D shown in various rotated configurations where the middle and distal segments rotate as the proximal segment rotates due to interaction of the links.

FIGS. 6A-6D are sequential views of the prosthetic digit of FIGS. 4A-4D shown in various rotated configurations where the middle and distal segments rotate as the proximal segment rotates due to interaction of the links.

FIGS. 7A-7D are sequential views of the prosthetic digit of FIGS. 4A-4D shown in various rotated configurations where the middle and distal segments rotate independently of rotation of the proximal segment due to interaction of the links.

FIGS. 8A-8B are perspective and cross-sections views respectively of another embodiment of a prosthetic digit, having articulating proximal, middle and distal segments.

Figure 1A:
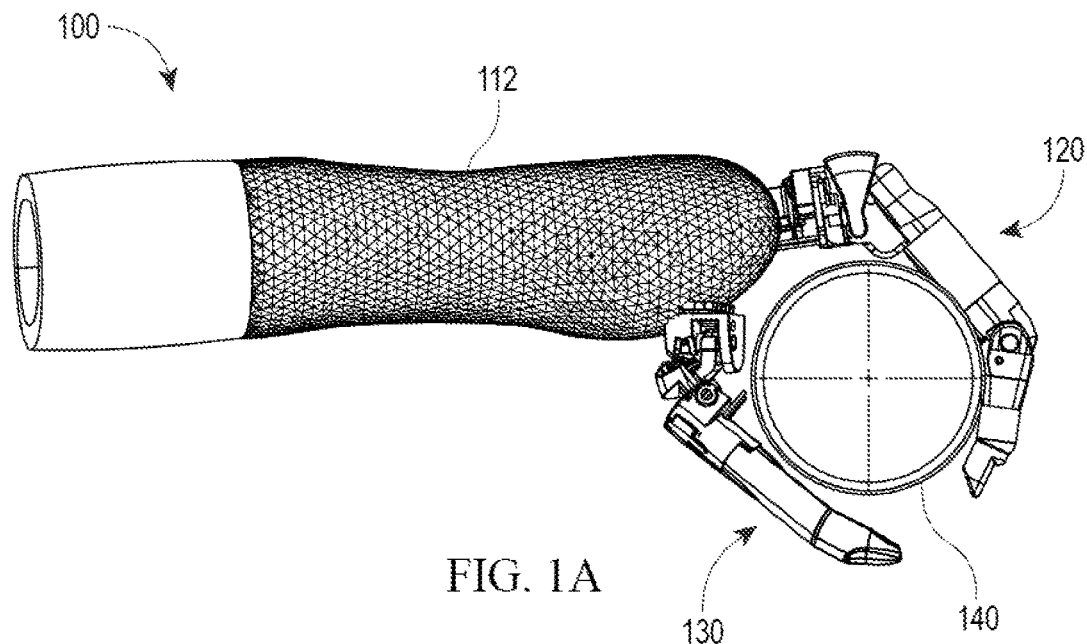
FIGS. 1A-1B are side and front views, respectively, of a lower arm stump having embodiments of prosthetic digits attached thereto, which prosthetic digits may be any of the prosthetic digits described herein.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

DETAILED DESCRIPTION

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

Features for prosthetic digits are described. The digits mimic natural fingers by having three articulating segments, including a proximal, middle and distal segment. The segments are articulated by an actuator and rotatably connected mechanical links configured to contribute to and/or cause rotation of the digit segments. Some versions may use one or more tendons to apply opening and closing forces to the digit. Other versions may not need a tendon to effect articulation of the segments. Rotation of a proximal segment causes rotation of the middle and distal segments via mechanical interaction of the links. There may be a proximal link and a distal link. The digit may have an actuator that outputs linear actuation to cause rotation of the proximal segment and/or proximal link. The actuator may linearly translate a housing that is rotatably connected to the proximal segment at a joint. The housing pushes on the proximal segment at the joint to create a torque on the segment about an offset pivot. The pivot may be a pin attaching the proximal segment to the proximal link. The pivot is at a location offset from the joint. In some embodiments, the proximal link may be linearly expandable and retractable to allow for variable relative rotational positions of the digit segments. The distal digit segment may rotate independent of rotation of the proximal digit segment. The digit may thus have multiple degrees of freedom with only a single actuator. The rotated digit may provide articulation that mimics a natural finger and thus fully surrounds both small and large objects to provide and restore enhanced gripping functionality to amputees. The digit provides space, weight and power savings due to the need for only a single actuator. The segments may provide movement similar to movement of respective human phalanges in sound natural fingers. In some embodiments, the digit includes transmission features for a worm wheel rotation by a lead screw. A keyed member such as a central axle is spring-biased and transmits rotation from the worm wheel to the digit while allowing for manual rotation of the digit without damaging the worm wheel or other components.

Figure 1B:
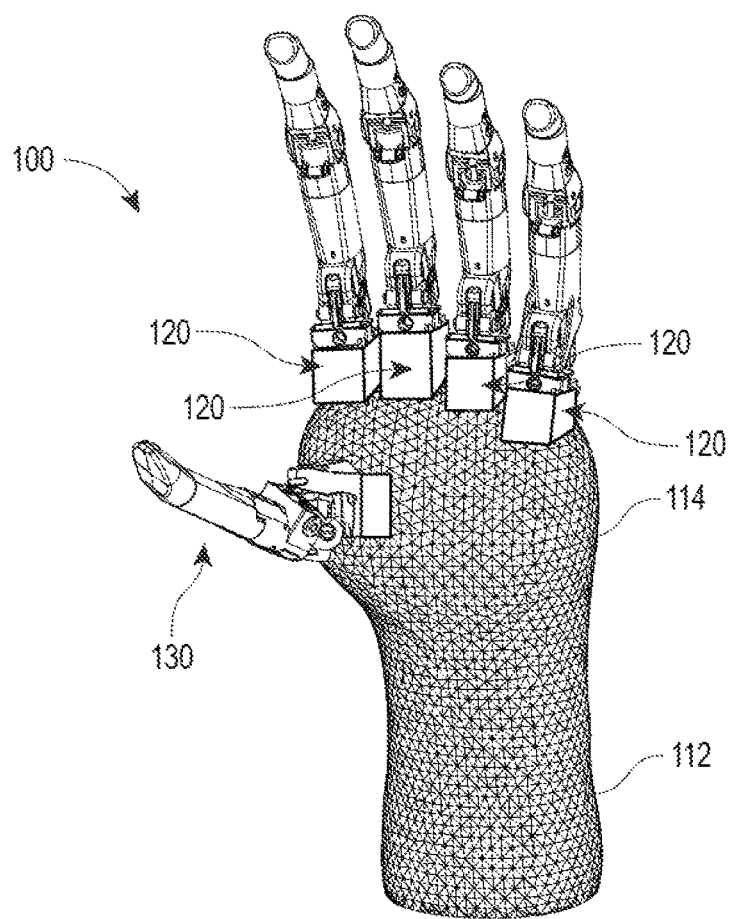

FIGS. 1A-1B are side and front views, respectively, of a lower arm prosthetic system 100 including a lower arm stump 112 having four prosthetic digits 120 and a prosthetic thumb 130 attached to the stump 112. FIG. 1A is a side view of the system 100. FIG. 1B is a front or palm-side view of the system 100. The prosthetic digits 120 and/or thumb 130 may be any of the prosthetic digits described herein. The digits 120 may be connected to the end of the lower arm stump 112, as shown in FIG. 1A, or to a residual natural palm 114, as shown in FIG. 1B.

As shown in FIG. 1A, the digits 120 and thumb 130 are grasping an object 140, shown as a round object such as a can or ball. The digits 120 are surrounding the object 140 such that the object 140 may be held securely by the system 100. The rotatable capability of the segments of the digits 120 allows for this secure grasp. The shape of the object 140 has a width and contour that allows the articulating digits 120 to provide a secure grasp. The digits 120 have various articulating segments that may rotate at various angles with respect to the adjacent segment. In some embodiments, the segments may rotate accordingly to a fixed angular relation, such that only certain sizes and shapes of objects 140 may be securely grasped. In some embodiments, the segments may rotate accordingly to a variable angular relation, such that only different sizes and shapes of objects 140 may be securely grasped.

Figure 2B:
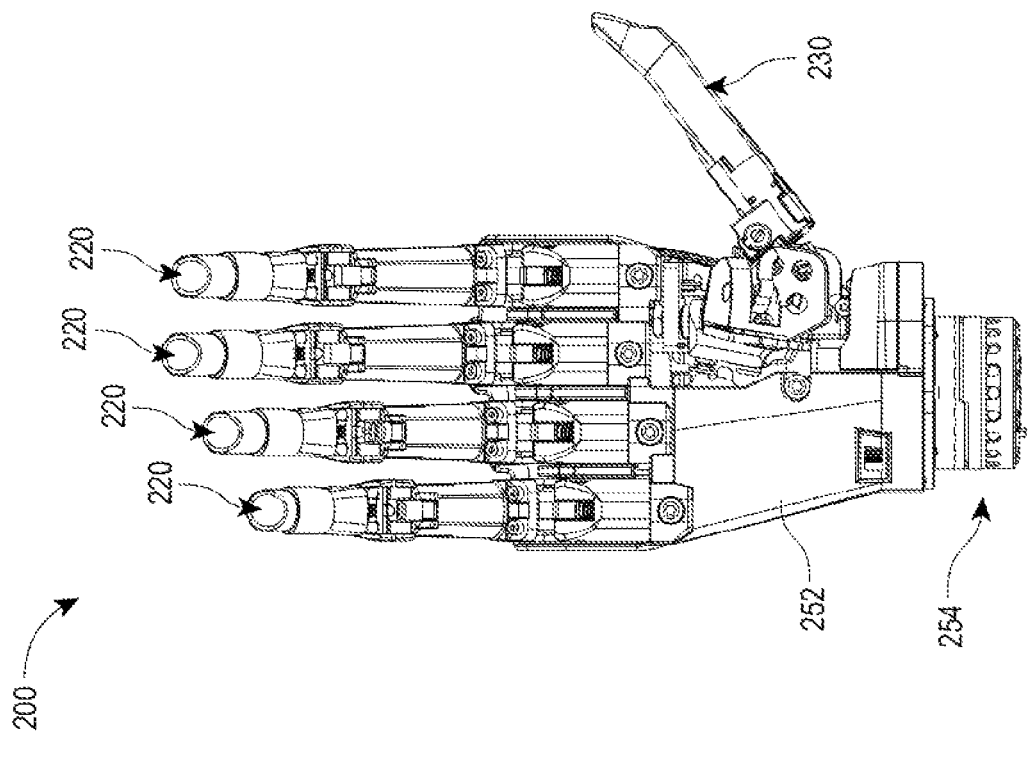
FIGS. 2A-2B are back and front views, respectively, of a prosthetic hand incorporating embodiments of prosthetic digits, which prosthetic digits may be any of the prosthetic digits described herein.
Figure 2A:
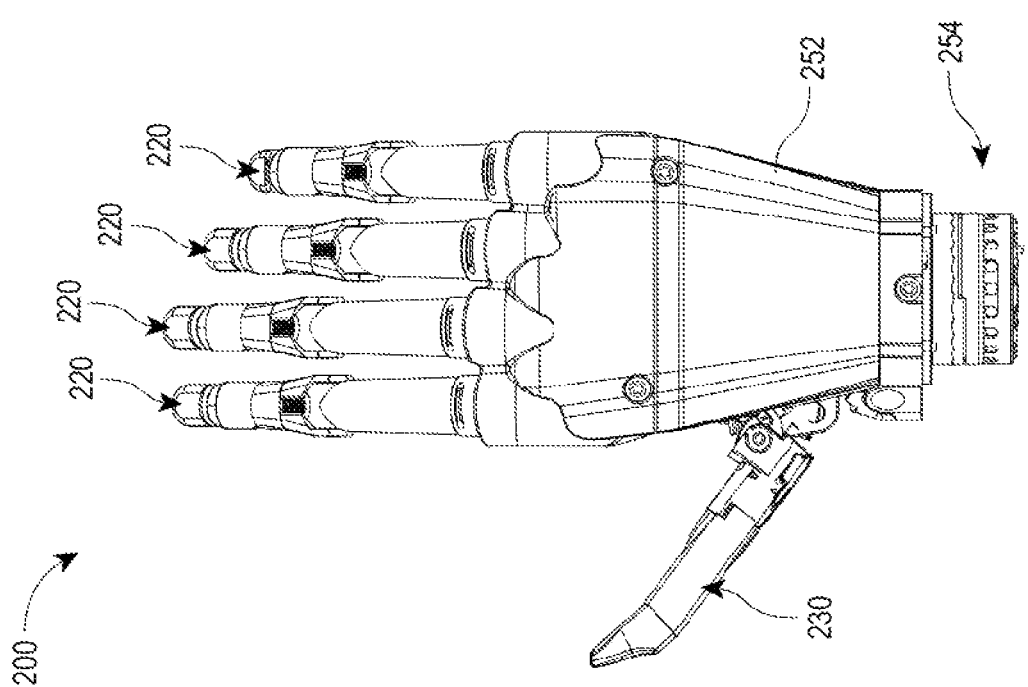

FIGS. 2A-2B are back and front views, respectively, of a prosthetic hand 200 incorporating embodiments of prosthetic digits 220 and a prosthetic thumb 230. The hand 200 has a palm portion 252 attached to proximal ends of the digits 220 and thumb 230. The hand 200 may have a wrist 254 that may rotate, which may allow for rotation of the palm portion 252, and the digits 220 and thumb 230 attached thereto, about a longitudinal axis defined by the wrist 254. The prosthetic digits 220 may be any of the prosthetic digits described herein. The prosthetic digits 220 may rotate according to a fixed or variable angular relation among the articulating digit segments, as described with respect to the system 100 of FIGS. 1A-1B.

FIGS. 3A-3D are various views of an embodiment of a prosthetic digit 300. The digit 300 may be used with the system 100 or hand 200. The digit 300 includes an actuator 301, a mount 350, a proximal segment 320, a middle segment 330, and a distal segment 340. The segments may articulate, for example rotate, relative to each other. The digit 300 includes mechanically-connected links, which may be rigid, as further described herein, for example with respect to FIGS. 3D-3G. The segments 320, 330, 340 may provide natural movement similar to that provided respectively by proximal, middle and distal phalanges of a sound natural finger.

The mount 350 and/or the actuator 301 may be connected with and/or located within, partially or completely, the arm stump 112, the residual palm 114, or the prosthetic palm 252. The proximal segment 320 may rotate relative to the mount 350 and/or the actuator 301. The middle segment 330 may rotate relative to the proximal segment 320. The distal segment 340 may rotate relative to the middle segment 330.

Figure 3A:
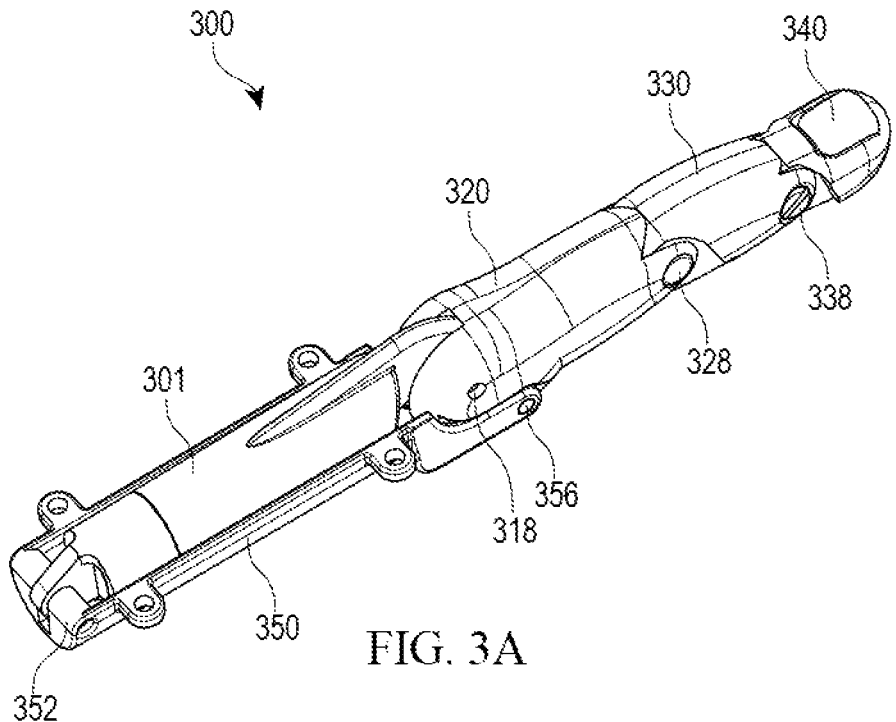
FIGS. 3A-3D are various views of an embodiment of a prosthetic digit, having articulating proximal, middle and distal segments and mechanically-connected rigid links, that may be used with the lower arm stump of FIGS. 1A-1B or prosthetic hand of FIGS. 2A-2B.
Figure 3B:
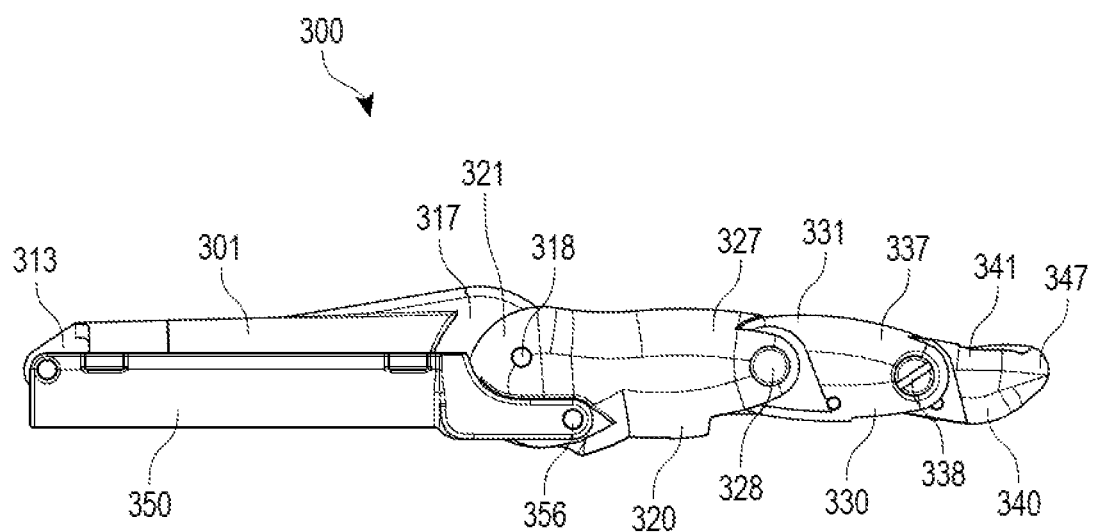

As shown in FIG. 3B, the actuator 301 includes a proximal end 313 and extends to a distal end 317. The proximal end 313 may attach to a hand, palm, etc. The distal end 317 attaches to a proximal end 321 of the proximal segment 320. The proximal segment 320 is rotatable relative to the actuator 301 about the joint 318. The actuator 301 may apply a normal force to the proximal segment 320 at the joint 318 to cause the proximal segment 320 to pivot about an offset first pivot 356, as further described herein. The proximal segment 320 extends from the proximal end 321 to a distal end 327. The distal end 327 attaches to a proximal end 331 of the middle segment 330. The middle segment 330 is rotatable relative to the proximal segment 320 about the joint 328. The middle segment 330 extends from the proximal end 331 to a distal end 337. The distal end 337 attaches to a proximal end 341 of the distal segment 340. The distal segment 340 is rotatable relative to the middle segment 330 about the joint 338. The rotatable connections at the joints 318, 328, 338 may include pin connections, hinges, and/or other suitable features for providing a rotatable engagement.

Figure 3C:
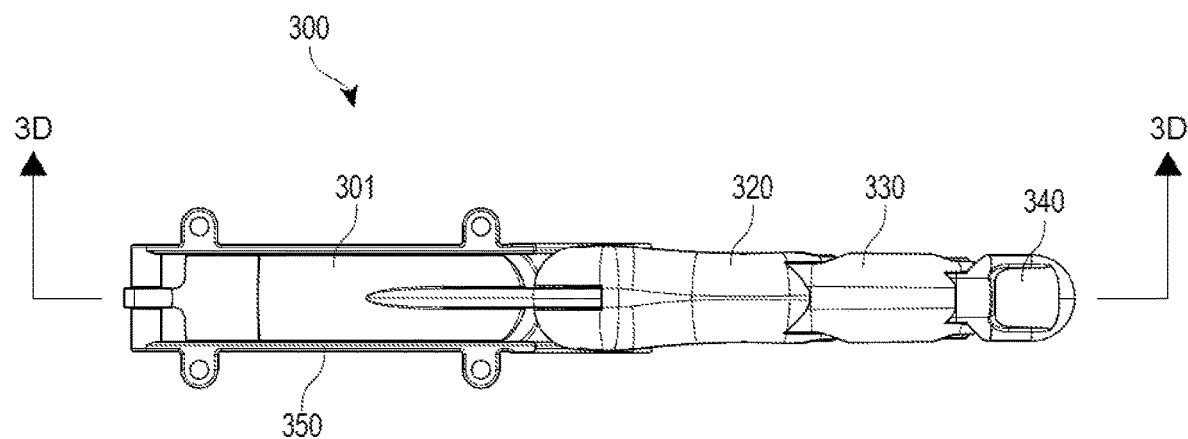
Figure 3D:
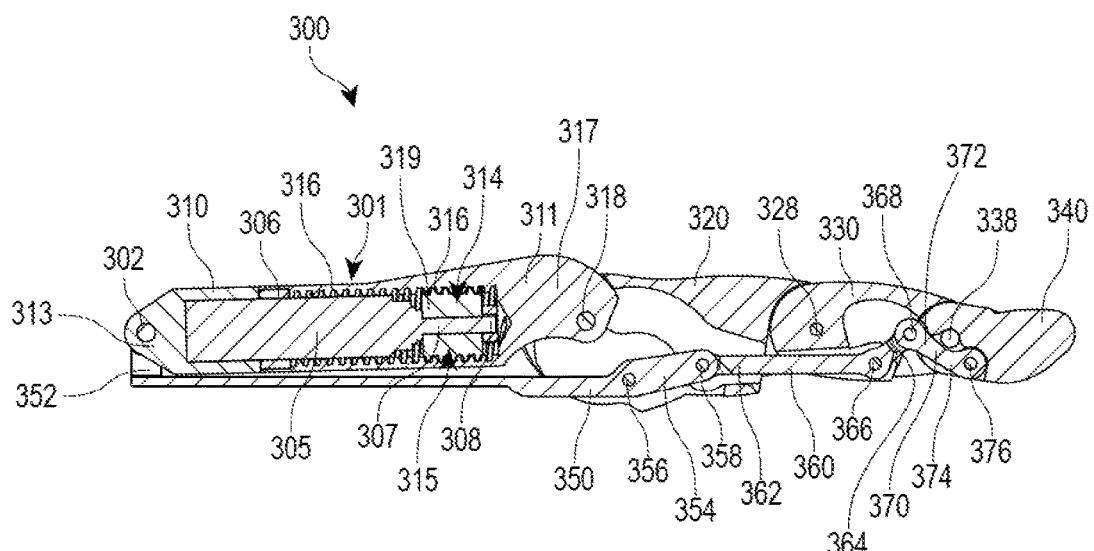

FIG. 3D is a cross-section view of the digit 300, as taken along the line 3D-3D indicated in FIG. 3C. As shown in FIG. 3D, the digit 300 may include the actuator 301. The actuator 301 may be a linear actuator. The actuator 301 produces or results in linear motion. As shown, the actuator 301 may include a motor 305 supplied with power from a battery, which may be in the hand or other location. A support 310, such as a motor mount or other structure, may carry or otherwise support the actuator 301. The support 310 may have a pin 302 or other suitable feature in a proximal end thereof to secure, for example rotatably attach, the support 310 with the mount 350.

The actuator 301 includes a housing 311. The housing 311 extends axially and defines a cavity 315 therein. The cavity 315 may be a cylindrical opening extending axially through the housing 311. A proximal end of the housing 311 may be open to the cavity 315. A distal end of the housing 311, for example at the distal end 317 of the actuator 301, connects with the proximal segment 320 at the joint 318. The housing 311 translates axially to cause rotation of the proximal segment 320, as further described herein.

The motor 305 may be supported, for example a fixed portion thereof, by the support 310. There may be a bushing 306 rotationally supporting a rotating portion of the motor 305, which may be located within and/or supported by the support 310. The motor 305 may include a shaft 307 extending therefrom, for example extending distally therefrom, that is rotated about an axis along which the shaft 307 extends. A cap 308, such as a nut, may attach to a distal end of the shaft 307. A leadscrew 314 having external threads 319 thereon may be positioned about the shaft 307 and secured in place by the cap 308. The leadscrew 314 may be a nut having external threads or other suitable features that engage corresponding internal structure of the housing 311 to translate the housing 311 back and forth.

The actuator 301 may output linear motion to cause rotation of the digit 300, as further described. The motor 305 or other portions of the actuator 301 may use or provide rotary, linear, cyclic and/or other types of motion. As shown, the actuator 301 is in mechanical communication with the leadscrew 314 having external threads 319. The actuator 301 rotates the leadscrew 314. The external threads 319 of the leadscrew 314 are in mechanical communication with internal threads 316 of the housing 311. The internal threads 316 may be located along the cavity 315 of the housing 311. The housing 311 may move relative to the support 310. The leadscrew 314 is rotated while remaining axially stationary to cause the housing 311 to translate axially along an axis defined by the cavity 315 via interaction of the external and internal threads 319, 316. The threaded engagement features and rotational motion of the actuator 301 is one example embodiment. Other features and/or actuator types may be used to output linear motion of the housing 311.

As the housing 311 is advanced distally and proximally, the actuator 301 may rotate about the pin 302 to accommodate the rotating proximal segment 320. For instance, the joint 318 may translate slightly during rotation, and the distal end of the housing 311 may move accordingly such that the actuator 301 rotates slightly at the pin 302. The actuator 301 may rotate counterclockwise as oriented in FIG. 3D during a distal movement of the housing 311 for a closing rotational movement of the segments 320, 330, 340. The actuator 301 may rotate clockwise as oriented in FIG. 3D during a proximal movement of the housing 311 for an opening rotational movement of the segments 320, 330, 340. Other configurations of the digit 300 may result in opposite rotations of the actuator 301 during opening and closing of the segments 320, 330, 340.

As further shown in FIG. 3D, the digit 300 includes a mount 350, a proximal link 360, and a distal link 370. The mount 350 extends from a proximal end 352 to a distal end 354. The proximal link 360 extends from a proximal end 362 to a distal end 364. The distal link 370 extends from a proximal end 372 to a distal end 374.

The proximal end 352 of the mount 350 may be attached to a proximal end of the actuator 301, for example rotatably attached thereto. The mount 350, such as at the proximal end 352 and/or other locations, may be attached to a hand, such as a prosthetic hand. Further details of the mount 350 are described herein, for example with respect to FIG. 3H. The distal end 354 of the mount 350 is rotatably attached to the proximal end 362 of the proximal link 360 about a connection 358. The mount 350 is also rotatably attached to the proximal segment 320 of the digit 300 about a first pivot 356. The first pivot 356 is located between the proximal and distal ends 352, 354 of the mount 350.

The proximal link 360 is rotatably attached to the middle segment 330 of the digit 300 about a second pivot 366. The second pivot 366 is located between the proximal and distal ends 362, 364 of the proximal link 360. The proximal link 360 may include a dogleg, where the proximal end 362 extends along a first axis and the distal end 364 extends along a second axis that is at an angle relative to the first axis. The second pivot 366 may be located at or near the vertex of the dogleg of the proximal link 360. The distal end 364 of the proximal link 360 is rotatably attached to the proximal end 372 of the distal link 370 about a connection 368. The distal end 374 of the distal link 370 is rotatably attached to the distal segment 340 of the digit 300 about a third pivot 376.

In sum, the digit segments 320, 330, 340 are, respectively, rotatably attached to the links 320, 330, 340 at, respectively, the pivots 356, 366, 376. The segments 320, 330, 340 are rotatably attached to each other at the joint 328, which rotatably connects the proximal segment 320 to the middle segment 330, and at the joint 338, which rotatably connects the middle segment 330 to the distal segment 340. The links 350, 360, 370 are rotatably attached to each other at the connection 358, which rotatably connects the mount 350 to the proximal link 360, and at the connection 368, which rotatably connects the proximal link 360 to the distal link 370.

All or some of the rotatable connections at the joints 318, 328, 338, at the pivots 356, 366, 376, and at the connections 358, 368 may include pins, hinges, and/or other suitable features for providing a rotatable engagement. The axes of rotation for the joints 318, 328, 338, pivots 356, 366, 376, and connections 358, 368 may be perpendicular to a longitudinal axis of the digit 300. Such longitudinal axis may be defined by the fully extended digit 300, for example as shown in FIG. 3F. The longitudinal axis may be defined by the direction of linear movement provided by the actuator 301, for example the direction of linear movement of the leadscrew 314. The rotation axes for the joints 318, 328, 338, pivots 356, 366, 376, and connections 358, 368 may be parallel to each other. The locations of the joints 318, 328, 338, pivots 356, 366, 376, and connections 358, 368 may change as the digit 300 rotates, for example some or all of these the locations may change relative to the support 310 and/or relative to the mount 350.

Figure 3E:
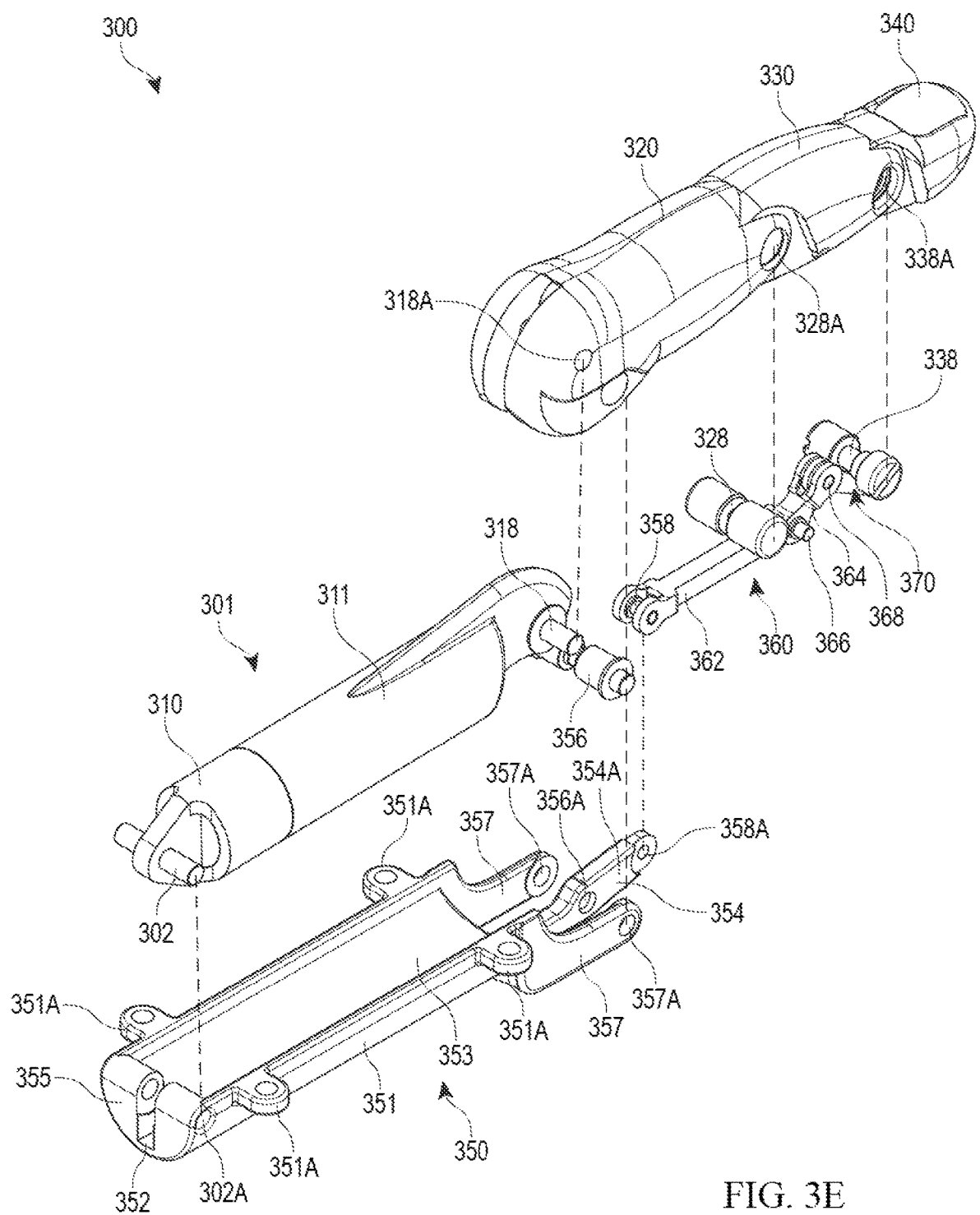
FIG. 3E is a partially exploded perspective view of the prosthetic digit of FIGS. 3A-3D.

FIG. 3E is a partially exploded perspective view of the prosthetic digit 400. As shown, the mount 350 includes an elongated proximal portion 351 defining a cavity 353 therein. The proximal end 352 includes a proximal wall 355 having openings 302A extending therethrough. The pin 302 of the support 310 may extend through the openings 302A to rotatably connect the proximal ends of the actuator 301 and mount 350. This allows the actuator 301 to rotate slightly at the proximal end as needed for digit actuation. The mount 350 includes a series of tabs 351A to connect the mount 350 to a hand, such as the prosthetic hand 200 or the palm 114. The mount 350 may fixedly attach to the hand. There may be four tabs 351A as shown, or more or fewer than four. The mount 350 includes two distally extending forks 357. The forks 357 extend from the distal end of the portion 351. The forks 357 define a space therebetween that receives a proximal portion of the proximal segment 320. The forks 357 include openings 357A that receive therein the pivot 356. The pivot 356 is shown as a pin with rollers.

The mount 350 includes a prong 354A extending distally from the proximal end of the portion 351. The prong 354A is located between the forks 357. The prong 354A is at the proximal end 354 of the mount 350. The prong 354A includes an opening 356A therethrough that receives therein a central portion of the pivot 356. The pivot 356 may thus rotate within the openings 356A, 357A, and/or provide an axle about which the proximal segment 320 rotates. The prong 354A includes an opening 358A at a distal end thereof. The opening 358A receives therein the connection 358, shown as a pin. The connection 358 may thus rotate within the openings 358A, and/or provide an axle about which the proximal link 360 rotates, as described herein.

The actuator 301 includes the joint 318, shown as a pin. The joint 318 is received into openings 318A of the proximal segment 320. The joint 318 may be a shear pin that is pushed by the housing 311 axially to impart a force on the proximal segment 320 at the openings 318A. The joint 318 is offset from the pivot 356. Thus pushing on the joint 318 will create a torque on the proximal segment about the pivot 356. The axes of rotation of the joint 318 and pivot 356 may be parallel to each other.

The middle segment 330 includes one or more openings 328A which receives the joint 328 therein. The joint 328 is shown as a pin. The joint 328 may thus rotate within the openings 328A, and/or provide an axle about which the proximal and middle segments 320, 330 rotate, as described herein. The distal segment 340 includes one or more openings 338A which receives the joint 338 therein. The joint 338 is shown as a pin. The joint 338 may thus rotate within the openings 338A, and/or provide an axle about which the middle and distal segments 330, 340 rotate, as described herein.

FIGS. 3F-3H are sequential views of the prosthetic digit 300 shown in various rotated configurations. "Distal" and "proximal" as used herein have their usual and ordinary meaning. For clarity, the "distal" and "proximal" directions are indicated in FIG. 3F for the fully extended digit 300, and generally refer to a direction or portion of the digit 300 that is, respectively, farther from or closer to the proximal end 352 of the mount 350 along the length of the digit 300. FIG. 3F shows an embodiment of a fully straightened digit 300, FIG. 3G shows an embodiment of partially closed digit 300, and FIG. 3H shows an embodiment of a fully closed digit 300.

The middle and distal segments 330, 340 may rotate as the proximal segment 320 rotates due to interaction of the mount 350 and links 360, 370 as further described. As shown, for example in FIG. 3H, the distal segment 340 may completely close such that the distal segment 340 is parallel or near parallel with the proximal segment 320. In some embodiments, the distal segment 340 may rotate through this parallel position such that at full rotation the distal segment 340 is angled back toward the proximal segment 320. The distal segment 340 may contact the proximal segment 320 in the fully rotated configuration. Such full or more complete closure of the distal segment 340 provides advantageous gripping capability with the digit 300 and more fully restores lost sound finger dexterity to a user, such as an amputee. The features described herein, such as the configuration and interaction of the mount 350, links 360, 370 and segments 320, 330, 340, among other things, contribute to such advantages.

To cause rotation of the digit 300, the actuator 301 may rotate the leadscrew 314 having the external thread. The external threads of the leadscrew 314 mechanically communicate with internal threads 316 of the housing 311. The actuator 301 may rotate the leadscrew 314 in a first rotational direction to cause the housing 311 to move, for example to translate, distally relative to the leadscrew 314. The leadscrew 314 may remain axially stationary. The housing 311 moves farther distally as shown sequentially from FIG. 3F to FIG. 3G to FIG. 3H. The direction of rotation of the digit 300 may be reversed (e.g., from FIG. 3H to FIG. 3G to FIG. 3F) by the actuator 301 rotating the leadscrew 314 in a second rotational direction, that is opposite to the first rotational direction, to cause the housing 311 to move, for example to translate, proximally relative to the leadscrew 314.

Distal movement of the housing 311 causes the proximal end 321 of the proximal segment 320 to move distally via the rotatable connection at the joint 318. Distal movement of the proximal segment 320 at the joint 318 will cause the proximal segment 320 to rotate clockwise (as oriented in the figures) about the first pivot 356 due to the offset locations of the joint 318 and the pivot 356. A line of action of force is imparted on the proximal segment 320 that extends through the joint 318 and thus imparts a moment on the proximal segment 320 about the pivot 356. The clockwise rotation of the proximal segment 320 about the first pivot 356 causes clockwise rotation of the proximal segment 320 relative to the housing 311 about the joint 318. Thus, the proximal segment 320 rotates clockwise as shown sequentially viewed from FIG. 3F to FIG. 3G to FIG. 3H. To reverse the direction of rotation in the counterclockwise direction (as oriented in the figures), these movements may be reversed, where the housing 311 is moved proximally to cause the proximal end 321 of the proximal segment 320 to move proximally and rotate counterclockwise about the first pivot 356 and the joint 318. A pinned or other type connection at the joint 318 as described herein may allow for such pushing and pulling forces by the housing 311 to be transferred to the proximal segment 320.

As the proximal segment 320 rotates clockwise about the pivot 356, the middle segment 330 also rotates clockwise with the rotating proximal segment 320 due to the connection of the two segments 320, 330 at the joint 328. In some embodiments, the middle segment 330 may be constrained from rotating farther in the counterclockwise direction, for instance the configuration shown in FIG. 3F may be the limit of rotation of the middle segment 330 relative to the proximal segment 320 about the joint 328.

The rotation of the middle segment 330 also causes the distal segment 340 to rotate clockwise, due to the connection of the two segments 330, 340 at the joint 368. In some embodiments, the distal segment 340 may be constrained from rotating farther in the counterclockwise direction, for instance the configuration shown in FIG. 3F may be the limit of rotation of the distal segment 340 relative to the middle segment 330 about the joint 338.

As the middle segment 330 rotates clockwise, the proximal link 360 also rotates clockwise due to the connection of the middle segment 330 and the proximal link 360 at the second pivot 366. Further, the proximal link 360 is translationally constrained by the mount 350 at the rotatable connection 358. The proximal link 360 thus rotates clockwise about the connection 358. The joint 328 is offset from the second pivot 366 as shown. Thus a torque may be imposed on the middle segment 330 about the pivot 366. The axes of rotation of the joint 328 and second pivot 366 may be parallel.

As the proximal link 360 rotates clockwise about the connection 358, this also causes the distal link 370 to rotate clockwise due to the translational constraint between the proximal link 360 and the distal link 370 at the rotatable connection 368. As the distal link 370 rotates clockwise, the distal segment 340 is translationally constrained by the distal link 370 at the third pivot 376. The distal segment 340 also rotates relative to the middle segment 330 about the rotatable connection at the joint 338. The joint 338 is offset from the third pivot 376 as shown. Thus, a torque may be imposed on the distal segment 340 about the pivot 376. The axes of rotation of the joint 338 and third pivot 376 may be parallel. The distal segment 340 thus rotates farther clockwise about the third pivot 376 to provide the closed configuration shown in FIG. 3H.

The digit 300 may be rotated in the counterclockwise direction sequentially from the configurations shown in FIG. 3H to FIG. 3G to FIG. 3F. The counterclockwise rotation operates in reverse as described above with respect to the clockwise rotation. For example, proximal movement of the proximal end 321 of the proximal segment 320 pulls proximally at the joint 318 and causes the proximal segment 320 to rotate counterclockwise about the pivot 356, which causes the middle segment 330 and proximal link 360 to rotate counterclockwise respectively about the joint 328 and pivot 366, which causes the distal segment 340 and distal link 370 to rotate counterclockwise respectively about the joint 338 and pivot 376.

FIGS. 4A-4D are various views of another embodiment of a prosthetic digit 400. The digit 400 may be used with the system 100 or hand 200. The digit 400 includes a mount 410, a proximal segment 420, a middle segment 430, and a distal segment 440. The mount 410 and segments 420, 430, 440 may have the same or similar features and/or functions as the mount 350 and segments 320, 330, 340, and thus may articulate, for example rotate, relative to each other. The digit 400 includes mechanically-connected rigid links including an expandable proximal link 450, as further described herein, for example with respect to FIGS. 4D-7D.

The mount 410 and segments 420, 430, 440 may be rotatably attached at joints 418, 428, 438, which may have the same or similar features and/or functions as the joints 318, 328, 338, respectively. However, the mount 410 may not have a linearly translatable portion. The digit 400 may have an actuator 404, which may have the same or similar features and/or functions as the actuator 301, except as otherwise described.

Figure 4A:
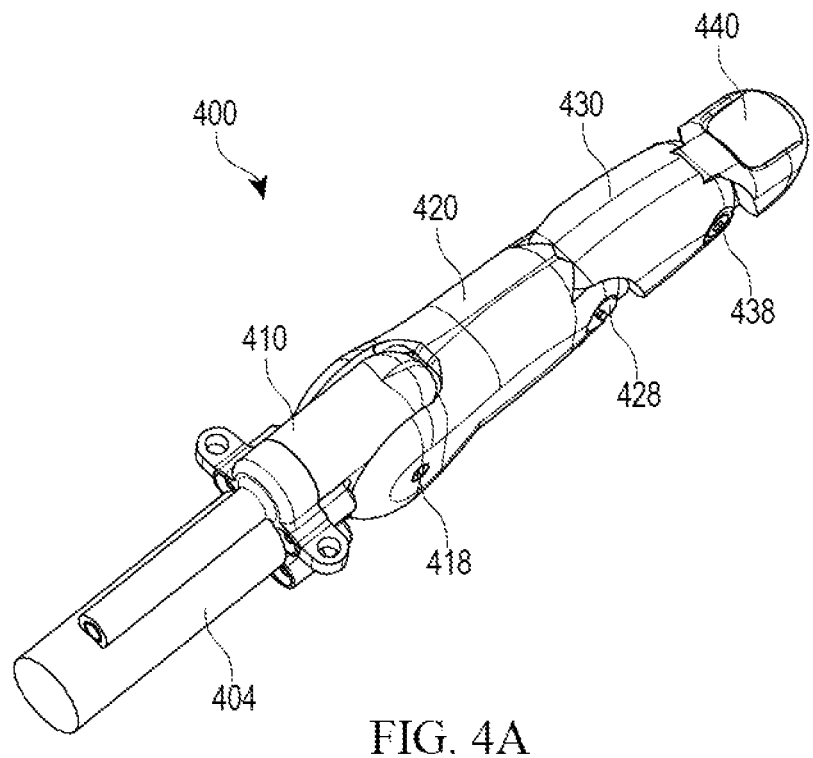
FIGS. 4A-4D are various views of another embodiment of a prosthetic digit, having articulating proximal, middle and distal segments and an expandable proximal link, that may be used with the lower arm stump of FIGS. 1A-1B or prosthetic hand of FIGS. 2A-2B.
Figure 4B:
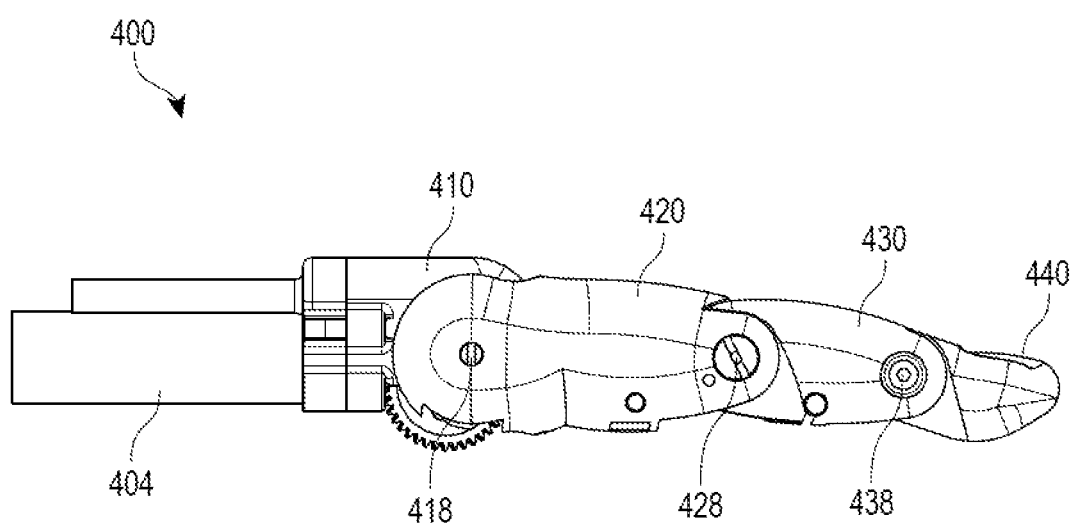
Figure 4C:
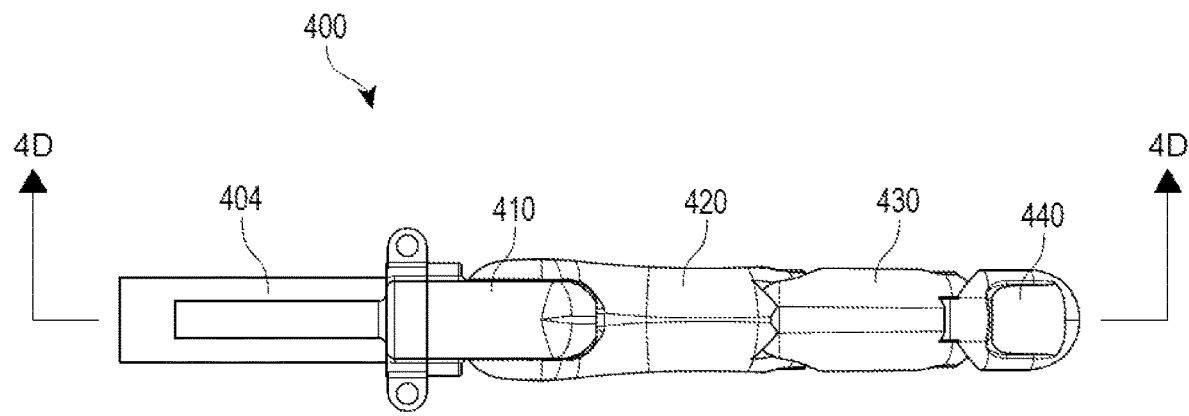
Figure 4D:
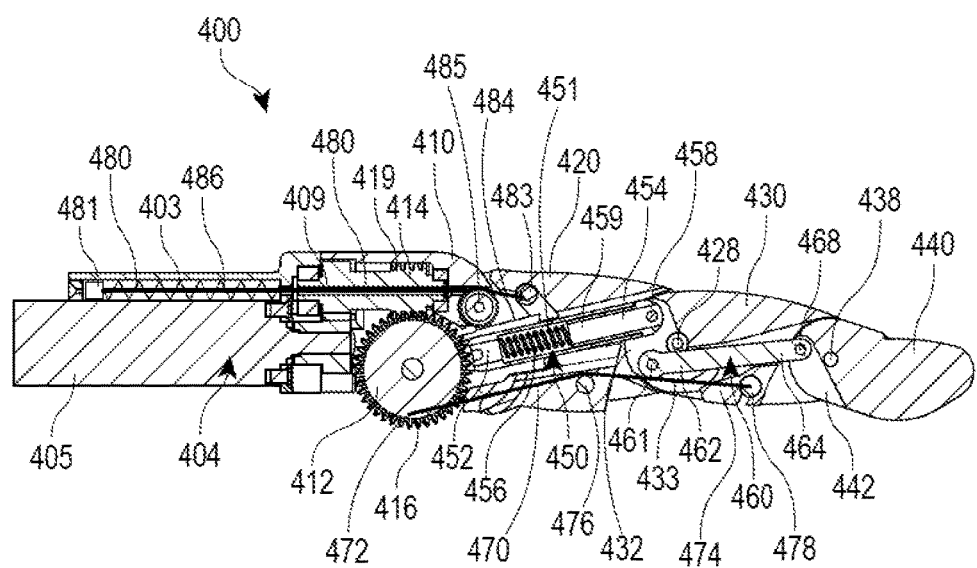

FIG. 4D is a cross-section view of the digit 400, as taken along the line 4D-4D indicated in FIG. 4C. As shown in FIG. 4D, the mount 410 may support the actuator 404. The actuator 404 may include a housing 403 extending proximally. The housing 403 may be used to house features for rotation of the segments 420, 430, 440, such as a spring 486 that provides a force in a proximal direction on a plunger 481 attached to a proximal end 482 of a return tendon 480, as further described herein. Some embodiments may not include the return tendon 480.

The actuator 404 may include a motor 405 supplied with power from a battery, which may be in the hand or other location. The motor 405 may be in mechanical communication with an output shaft 409 that extends, for example distally, therefrom. A worm gear 414 having external threads 419 thereon may be attached to the shaft 409. Actuation of the motor 405 causes motion to be transmitted via a gearbox to the shaft 409 to rotate the worm gear 414. The digit 400 may include a worm wheel 412 having external teeth 416 thereon. The threads 419 of the worm gear 414 contact the teeth 416 of the worm wheel 412 to cause rotational motion of the worm wheel 412. The worm wheel 412 may be rotated a first rotational direction to cause a first rotation of the digit 400 in a first direction (e.g. to close the digit 400). The worm wheel may have pulley features that attach to and wrapingly receive therearound a proximal end of an actuation tendon 470, as further described. The worm wheel 412 may be rotated in a second rotational direction that is opposite the first rotational direction to allow for a second rotation of the digit 400 in a second direction that is opposite the first direction (e.g. to open the digit), which movement may be caused by the return tendon 480, as further described. Some embodiments may not include the actuation tendon 470 or return tendon 480.

The digit 400 includes an expandable proximal link 450. The link 450 is attached to the worm wheel 412. Rotation of the worm wheel 412 in a first rotational direction for a first angular amount causes a corresponding rotation of the link 450 in the first rotational direction for the first angular amount. The link 450 may expand. The link 450 or a portion thereof may extend distally relative to the worm wheel 412. The link 450 includes a proximal end 452 and extends to a distal end 454. The proximal end 452 includes a fixed portion 451, such as a cylinder. The distal end 454 includes a housing 459, such as a piston. The link 450 may include a spring 456, such as an extension spring. Extension of the spring 456 beyond a neutral length may cause a restoring force that biases the spring back to a shorter length. The link 450 may expand as it is rotated to allow for multiple degrees of freedom rotation of the digit 40. The housing 459 may expand distally relative to the fixed portion 451. The spring 456 may bias the housing 459 in the proximal direction. The housing 459 may retract in the proximal direction relative to the fixed portion 451. Further details of the link 450 are described herein, for example with respect to FIGS. 5A-5E.

The link 450 is attached to the middle segment 430 of the digit 400. The distal end 454 of the link 450 may be rotatably attached to the middle segment 430 at the connection 458. The middle segment 430 may include an ear 432 that rotatably connects with the link 450. The connection 458 may include a pin or other feature that extends through the link 450 and ear 432 at the connection 458. The link 450 may extend between two of the ears 432, with one ear 432 on either lateral side of the distal end 454 of the link 450 at the connection 458.

The digit 400 may include a distal link 460. The distal link 460 extends from a proximal end 462 to a distal end 464. The proximal end 462 may be rotatably attached to the ear 432 at a connection 461. The ear 432 may include a rounded slot 433. The connection 461 may include a pin or other feature that extends through the link 460 and rounded slot 433 at the connection 461. The connection 461 allows the proximal end 462 of the distal link 460 to rotate within and move along the slot 433 as the digit 400 articulates, for example as the middle segment 430 rotates relative to the proximal segment 420 and/or as the distal segment 440 rotates relative to the middle segment 430.

The distal link 460 is attached to the distal segment 440. The distal end 464 of the distal link 460 may be rotatably attached to the distal segment 440 at the connection 468. The connection 468 may include a pin or other feature that extends through the distal link 460 and distal segment 440 at the connection 468. The distal segment 440 may include an ear 442 having an opening therethrough and with which the distal link 460 is attached. The distal end 464 of the link 460 may extend between two of the ears 442, with one ear 442 on either lateral side of the distal end 464 of the link 460 at the connection 468.

Figure 5A:
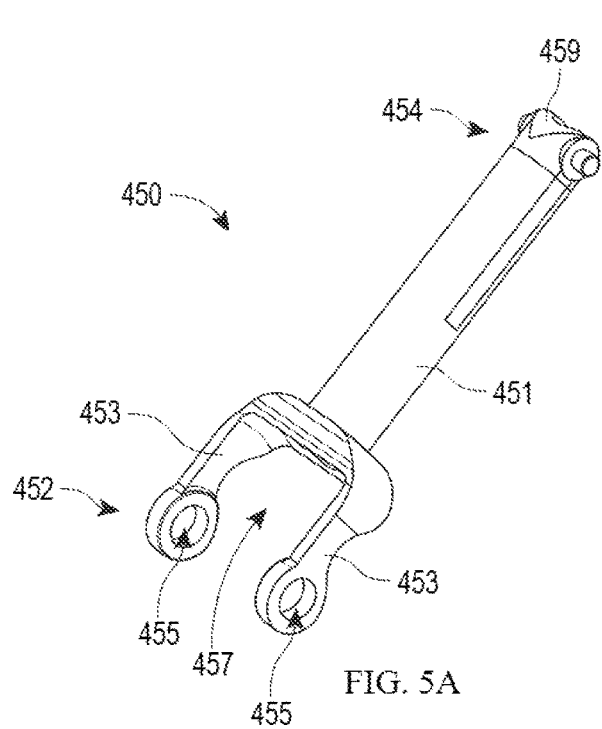
FIGS. 5A-5E are various views of the expandable link used in the prosthetic digit of FIGS. 4A-4D.
Figure 5B:
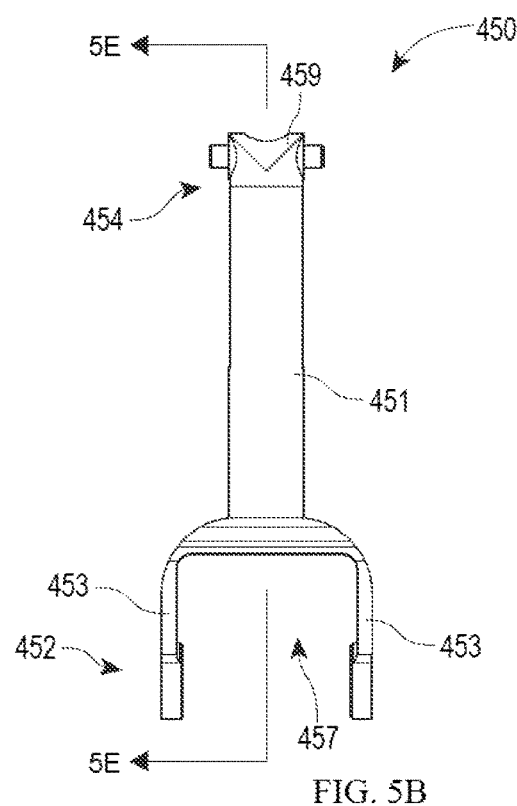
Figure 5C:
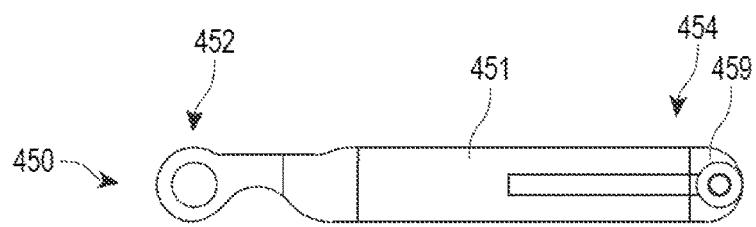
Figure 5D:
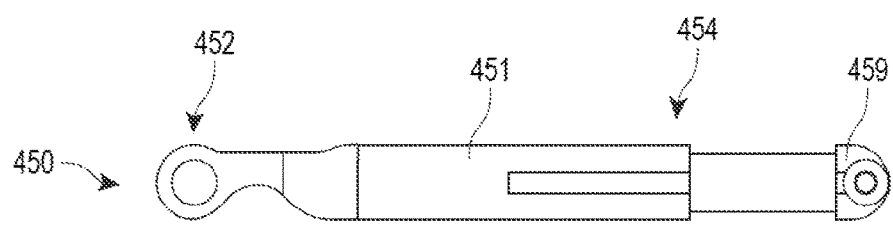
Figure 5E:
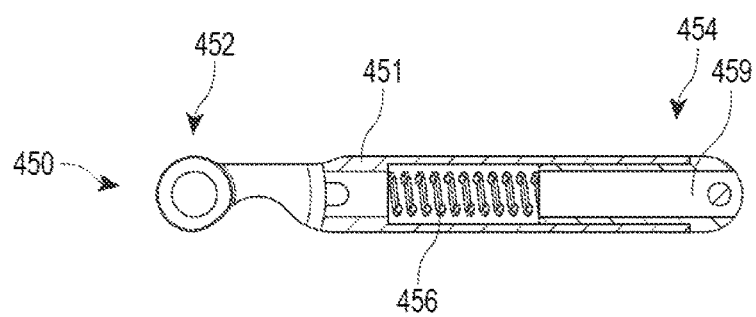

FIGS. 5A-5E are various views of the proximal expandable link 450. FIG. 5A is a perspective view of the link 450, FIG. 5B is a top view, FIG. 5C is a side view in an unexpanded configuration, FIG. 5D is a side view in an expanded configuration, and FIG. 5E is a cross-section view as taken along the line 5E-5E shown in FIG. 5B.

The proximal link 450 may include an extension 453. There may be two extensions 453 extending proximally, for example forming a clevis type connection. The extensions 453 may each include an opening 455 therethrough. The extensions 453 may define a space 457 therebetween. The extensions 453 may laterally surround the worm wheel 412 when installed with the worm wheel 412 located in the space 457, and a pin or other feature may extend through the openings 455 and a central opening of the worm wheel 412 to connect the link 450 with the worm wheel 412.

The housing 459 may move linearly with respect to the fixed portion 451. The fixed portion 451 may define a longitudinal axis along which the housing 459 may translate. A spring 456 may be located within the link 450. As shown in FIG. 5E, a proximal end of the spring 456 may be located within the fixed portion 451 and be attached to a proximal end of the link 450. A distal end of the spring 456 may attach to a proximal end of the housing 459. In some embodiments, the spring 456 may extend through and attach to the housing 459. FIG. 5D shows the link 450 expanded relative to the configuration in FIG. 5C. The expanded housing 459 will stretch the spring 456. The spring 456 will exert a restoring force on the housing 459 and bias the housing proximally. The link 450 may then return to the configuration shown in FIG. 5C. The link 450 may repeatedly extend and retract as the finger is rotated to close the digit 400 and then rotated back to open the digit 400. The link 450 may therefore expand during rotation of the digit 400, as further described herein, for example with respect to FIGS. 6A-6D. In some embodiments, the link 450 may not expand during rotation of the digit 400 for added degrees of freedom, as further described herein, for example with respect to FIGS. 7A-7D.

FIGS. 6A-6D are sequential views of the prosthetic digit 400 shown in various rotated configurations. The sequential views illustrate an embodiment of the middle and distal segments 430, 440 rotating as the proximal segment 420 also rotates. The rotation of the segments 420, 430, 440 may be due to the configuration and interaction of the mount 410, segments 420, 430, 440 and links 450, 460.

The proximal segment 420 may rotate relative to the mount 410 about the joint 418 (see FIGS. 4A-4B). To initiate rotation of the digit 400, the actuator 404 may cause the worm gear 414 to rotate and thereby rotate the worm wheel 412.

In some embodiments, the link 450 may rotate with the rotating worm wheel 412. The link 450 may rotate the same or similar angular amount as the angular amount that the worm wheel 412 rotates. For example, rotation of the worm wheel 412 by fifteen degrees clockwise may cause a corresponding fifteen degree rotation of the link 450, etc.

In some embodiments, rotation of the link 450 may cause the proximal segment 420 to rotate. For example, the link 450 may be attached with the proximal segment 420, such that rotation of the link 450 in a first or second rotational direction may cause a corresponding rotation of the proximal segment 420 in the first or second rotational direction, respectively.

In some embodiments, rotation of the worm wheel 412 may not cause the link 450 or proximal segment 420 to rotate. For example, the link 450 may be rotatably connected to the worm wheel. The middle and distal segments 430, 440 may thus rotate while the proximal segment 420 does not rotate or rotates less as compared to a full rotation, as further described with respect to FIGS. 7A-7D. In some embodiments, actuation of the digit segments may be provided by the actuation tendon 470 attached to the worm wheel 412 and to the various segments 420, 430, 440, such that rotation of the worm wheel 412 will cause the tendon to pull in (shorten) to cause rotation of the segments 420, 430, 440. The return tendon 480 may rotate the digit 400 in the opposite direction, as described herein, and the worm wheel 412 may rotate in the opposite direction to allow the actuation tendon to pay out (lengthen).

The digit 400 may include the actuation tendon 470. The tendon 470 extends from a proximal end 472 attached to the worm wheel 412 to a distal end 474 attached to an attachment 478 of the middle segment 430. The tendon 470 extends distally from the worm wheel 412 and around an idler 476, such as a pulley, which may or may not rotate, and that is connected to the proximal segment 420. As the worm wheel 412 rotates clockwise as oriented from FIG. 6A to FIG. 6D (also shown in FIGS. 7A to 7D), the proximal end 472 of the tendon 470 wraps around the worm wheel 412. The tendon 470 effectively shortens in length and thus pulls on the attachment 478 and applies a force on the idler 476, causing the middle and proximal segments, to which the attachment 478 and idler 476 are respectively attached, to rotate in the clockwise direction as oriented.

The digit 400 may include the return tendon 480. The return tendon 480 extends from a proximal end of the digit 400 and is attached to the plunger 481. The plunger 481 is biased in the proximal direction by a compression spring 486 inside the housing 403. The tendon 480 extends from the housing 403 in a distal direction around an idler 485, such as a pulley, which may or may not rotate, to a distal end 484 of the tendon 480 attached to an attachment 483 of the proximal segment 420. As the proximal segment 420 rotates clockwise as oriented, due to the actuation tendon 470 as described, the attachment 483 pulls on the return tendon 480 causing the plunger 481 to move distally and compress or further compress the spring 486. The spring 486 compresses further as the digit 400 rotates further clockwise. The spring 486 thus applies a biasing force in the proximal direction to the plunger 481, biasing the tendon 480 in the proximal direction, and applying an opening or counterclockwise force to the proximal segment 420 via the attachment 483. In some embodiments, the spring 486 may be a constant force spring to apply a constant return force to the segment 420 in various rotational positions.

As the worm wheel 412 is rotated counterclockwise as oriented to effectively lengthen or pay out the actuation tendon 470, the biasing force on the return tendon 480 causes the proximal segment 420 to rotate open, or in the counterclockwise direction as oriented. Further, the spring-loaded expandable link 450, as described herein, then pulls proximally on the middle segment 430 at the connection 458 to rotate the middle segment 430 counterclockwise about the joint 428. The ear 432 may then rotate counterclockwise about the joint 428 to rotate the connection 461 of the distal link 460 counterclockwise about the joint 428 to rotate the distal segment 440 counterclockwise as well.

The tendons 470, 480 are just one example of how to effect articulation of the segments 420, 430, 440 in the prosthetic digit 400 having the expandable link 450. Some embodiments of the digit 400 having the expandable link 450 may not include the actuation tendon 470 and/or the return tendon 480. For example, features other than tendons may be used, such as other links, connections, joints, segments, etc. Therefore, the embodiments shown and described herein for articulation of the segments 420, 430, 440 are merely example embodiments of how the prosthetic digit 400 with the expandable link 450 may be implemented.

As the link 450 rotates, the rotatable connection 458 of the link 450 with the middle segment 430 translates or sweeps a rotational path. The middle segment 430 is translationally constrained with the distal end 459 of the link 450 at the connection 458. The middle segment 430 thus rotates relative to the link 450 about the connection 458 as the middle segment 430 is rotating to open or close the digit 400. The middle segment 430 also rotates relative to the proximal segment 420 about the joint 428 (see FIGS. 4A-4B).

As the middle segment 430 rotates, the connection 461 at the proximal end 462 of the distal link 460 moves along the slot 433. The connection 461 may include a pin sliding along the slot 433. This allows the ear 432 to rotate relative to the distal link 460. The distal link 460 thus rotates relative to the middle segment 430. As the distal link 460 rotates, the distal segment 440 also rotates due to the connection 468 between the distal link 460 and the distal segment 440. The distal segment 440 rotates relative to the middle segment 430 about the joint 438.

As shown in FIGS. 6B and 6D, the mount 410 or a portion thereof may extend along an Axis 1. The proximal segment 420 may extend along an Axis 2. The Axes 1,2 may form an angle A between them. The angle A may be the angular configuration of the proximal segment 420 relative to the mount 410. The angle A may range from zero degrees (e.g., in FIG. 6A) to ninety degrees or more (e.g., in FIG. 6D). In some embodiments, the angle A may be negative fifteen, negative ten, negative five, zero, five, ten, fifteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred five, one hundred ten, or one hundred fifteen degrees, or other lesser, greater or in between angular amounts. The various values for the angle A may apply to any of the articulated configurations of the prosthetic digit 400 shown in any of FIGS. 6A-6D and other configurations.

The angle A may change as the digit 400 rotates, for example as the middle and distal segments 430, 440 rotate. As shown, the angle A may increase from the relatively open configuration of FIG. 6B to the relatively closed configuration of FIG. 6D, and vice versa. The angle A may be dependent on the amount of rotation of the middle and distal segments 430, 440, or vice versa. In some embodiments, the angle A may not change as the digit 400 rotates, for example as the middle and distal segments 430, 440 rotate. For example, the angle A may not change from the relatively open configuration of FIG. 6B to the relatively closed configuration of FIG. 6D, and vice versa. In some embodiments, the angle A may change by a small amount from the relatively open configuration of FIG. 6B to the relatively closed configuration of FIG. 6D, and vice versa, for example by five degrees or less, ten degrees or less, fifteen degrees or less, or twenty degrees or less. The angle A therefore may not be dependent on the amount of rotation of the middle and distal segments 430, 440, or vice versa, as further described herein, for example with respect to FIGS. 7A-7D.

The digit 400 may rotate as described to have the closed configuration shown in FIG. 6D. The Axis 2 along which the proximal segment 420 extends may be at about ninety degrees to the Axis 1. The middle segment 430 may be rotated to about parallel with the Axis 1. In some embodiments, the middle segment 430 may not be parallel with the Axis 1 in the closed configuration. As also shown, the distal segment 440 is rotated clockwise to be adjacent to the proximal segment 420. The segments 420, 430, 440 may thus rotate to provide a small, closed grip with the digit 400.

FIGS. 7A-7D are sequential views of the prosthetic digit 400 performing a rotation with added degrees of freedom. The digit 400 is shown in various rotated configurations where the middle and distal segments 430, 440 rotate independently of rotation of the proximal segment 420 due to interaction of the links 450, 460. The digit 400 may rotate similarly as described with respect to FIGS. 6A-6D, except as otherwise described.

In some embodiments, the digit 400 may rotate to grab or cover an object having an irregular outer surface or contour. The rotational path of the digit 400 shown in FIGS. 6A-6D may not adequately cover or grasp the object due to the irregular outer surface. Thus the proximal and/or middle segments 420, 430 may be prevented from rotating clockwise beyond an angular amount. In such case, the middle and/or distal segments 430, 440 may continue to rotate to provide the desired functionality. FIGS. 7A-7D shown an example embodiment of rotation of the digit 400 where the proximal segment 420 does not rotate or does not completely rotate clockwise, while the middle and distal segments 430, 440 rotate clockwise.

As the digit 400 rotates from FIG. 7A to FIG. 7D, the proximal segment 420 may be prevented from rotation. This may be due to a force exerted on the proximal segment 420 by an outside object that counteracts the closing direction, such as contact with a part of the object the digit 400 is grasping. The middle and distal segments 430, 440 may continue to rotate due to the link 450 expanding. The link 450 as shown may elongate as the digit 400 rotates. The housing 459 may extend distally away from or proximally toward the fixed portion 451 as the digit 400 is rotated clockwise or counterclockwise, respectively. As shown in FIG. 7D, the angle A between the Axes 1 and 2 may therefore not change, or may change by a small amount, as described herein, for example with respect to FIGS. 6A-6D.

The link 450 may have a first axial length in FIG. 7A for instance where the digit 400 is straightened out, a second axial length in FIG. 7B where the digit 400 has partially rotated, a third axial length in FIG. 7C where the digit 400 is rotated farther but not completely, and a fourth axial length in FIG. 7D where the digit 400 is fully rotated. The first length may be shorter than each of the second, third and fourth lengths. The second length may be shorter than each of the third and fourth lengths. The third length may be shorter than the fourth length.

The middle and distal segments 430, 440 rotate as described with respect to FIGS. 6A-6D. The expanding and retracting link 450 allows the middle and distal segments 430, 440 to rotate without rotation or full rotation of the proximal segment 420. In some embodiments, the link 450 may not rotate. In some embodiments, the link 450 may partially rotate. In some embodiments, a tendon may be used to cause rotation of the middle and distal segments 430, 440 when the proximal segment 420 does not rotate or does not fully rotate. A tendon may be attached to the worm wheel 412 to cause rotation, as described with respect to FIGS. 6A-6D.

FIGS. 8A-8B are various views of another embodiment of a prosthetic digit 500. The digit 500 may be used with the system 100 or hand 200. The digit 500 includes a mount 510, a proximal segment 520, a middle segment 530, and a distal segment 540. The mount 510 and segments 520, 530, 540 may have the same or similar features and/or functions as respectively the mounts 350, 450 and segments 320, 330, 340, 420, 430, 440, and thus may articulate, for example rotate, relative to each other, etc.

The digit 500 includes mechanically-connected rigid links, including a proximal link 560 and a distal link 570. The links 560, 570 may have the same or similar features and/or functions as the links 360, 370. For example, the mount 510 may be rotatably attached to the proximal end of the proximal link 560 about a connection 558. The proximal link 560 is rotatably attached to the middle segment 530 of the digit 500 about a pivot 566. The proximal link 560 may include a dogleg, where the proximal end of the proximal link 560 extends along a first axis and the distal end of the proximal link extends along a second axis that is at an angle relative to the first axis. The pivot 566 may be located at or near the vertex of the dogleg of the proximal link 560. The distal end of the proximal link 560 is rotatably attached to the proximal end of the distal link 570 about a connection 568. The distal end of the distal link 570 is rotatably attached to the distal segment 540 of the digit 500 about a pivot 576.

The digit 500 includes an actuator 504, which may have the same or similar features and/or functions as the actuators 301, 404, except as otherwise described. For example, the actuator 504 may include a motor 515 supplied with power from a battery, which may be in the hand or other location. The motor 515 may have an output shaft that extends, for example distally, therefrom, and that mechanically communicates with an off-axis shaft 509.

The actuator 504 includes a worm wheel 512 and a worm gear 514, which may have the same or similar features and/or functions as respectively the worm wheel and worm gear 412, 414, except as otherwise described. For example, the worm gear 514 having external threads 519 thereon may be in mechanical communication with the shaft 509 via the threads 519. Actuation of the motor 515 causes motion to be transmitted via a pinion gear 513 (see FIGS. 9B and 9C) to the shaft 509 to rotate the worm gear 514. The worm wheel 512 may have external teeth 516 thereon. In some embodiments, only a portion of the outer circumference of the worm wheel 512 includes external teeth 516 (e.g., the portion of the outer circumference of the worm wheel 512 positioned adjacent to the worm gear 514). The remainder of the outer circumference of the worm wheel 512 may be smooth or otherwise not have teeth. This configuration can advantageously allow for a compact worm wheel 512 and worm gear 514 system. The threads 519 (see FIGS. 9B and 9C) of the worm gear 514 contact the teeth 516 of the worm wheel 512 to cause rotational motion of the worm wheel 512. The worm wheel 512 may be rotated a first rotational direction to cause a first rotation of the digit 500 in a first direction (e.g. to close the digit 500). The worm wheel 512 may be rotated in a second rotational direction that is opposite the first rotational direction to allow for a second rotation of the digit 500 in a second direction that is opposite the first direction (e.g. to open the digit).

Figure 9A:
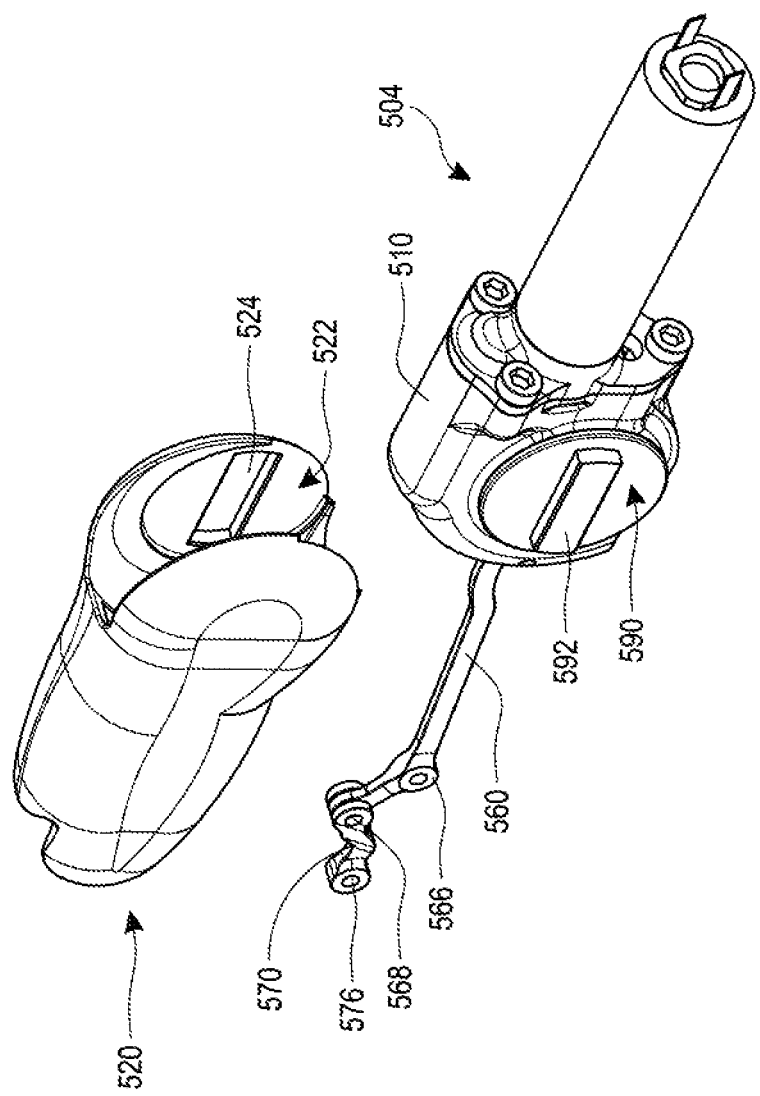
FIGS. 9A-9C are various views of the actuator of the prosthetic digit of FIGS. 8A-8B.
Figure 9C:
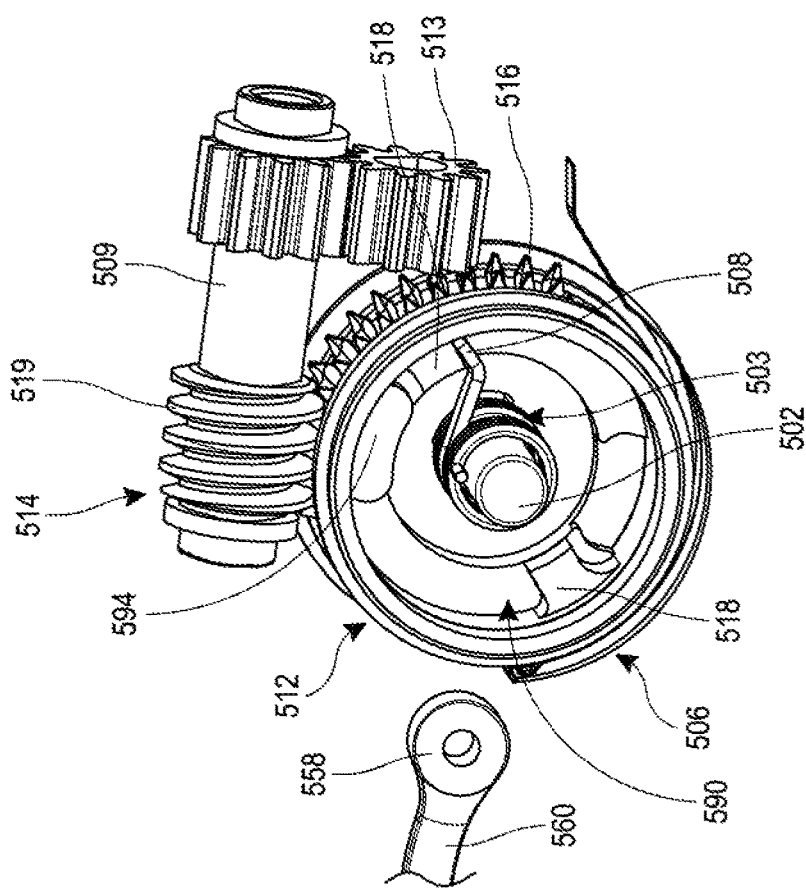
Figure 9B:
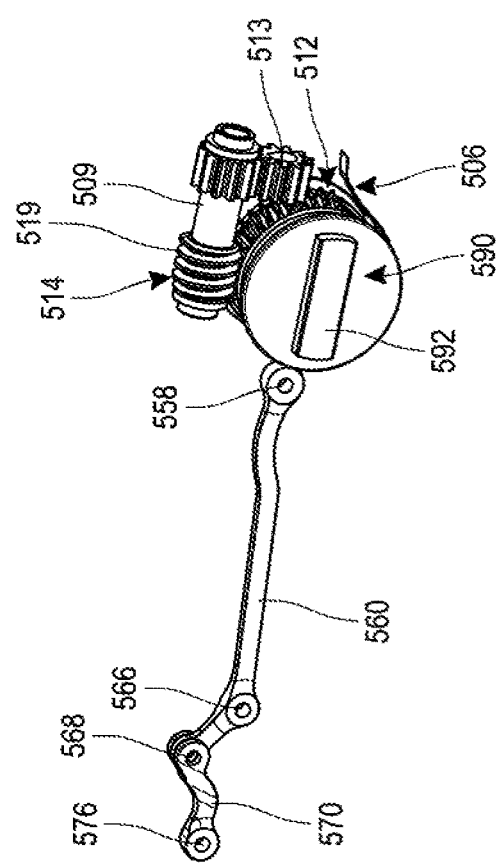

FIGS. 9A-9C are various views of the actuator 504 of the digit 500. FIG. 9A is a partial exploded view of the actuator 504, and FIGS. 9B and 9C show the actuator 504 with various features removed or hidden for clarity. The actuator 504 of the digit 500 may comprise a central axle 590 having a drive key 592 configured to engage a portion of the proximal segment 520 of the digit 500. For example, in some embodiments, the drive key 592 is positioned on an outer surface of the central axle 590 and has an extended length and width protruding outwardly from the outer surface of the central axle 590. An inner surface 522 of the proximal segment 520 of the digit 500 may comprise a mating feature 524, such as a recess, opening, and/or groove, with a shape that corresponds with the shape of the drive key 592 of the central axle 590. The mating feature 524 of the proximal segment 520 may receive the drive key 592 of the central axle 590 therein to transmit a rotational force from the central axle 590 to the proximal segment 520. In some embodiments, the ratio of the rotational angle of the drive key 592 to the rotational angle of the proximal segment 520 is 1:1.

In some embodiments, the central axle 590 includes a first drive key 592 protruding outwardly in a first direction from a first outer surface of the central axle 590 and a second drive key 592 protruding outwardly from a second outer surface of the central axle 590 in a second direction that is opposite the first direction. The proximal segment 520 may include a first inner surface 522 with a first mating feature 524 for receiving the first drive key 592 and a second inner surface 522 with a second mating feature 524 for receiving the second drive key 592.

In some embodiments, the central axle 590 may include one or more drive tabs 594. The drive tabs 594 may each have an extended, arcuate length and width protruding axially from an inner surface of the central axle 590. In some embodiments, the central axle 590 includes a first drive tab 594 and a second drive tab 594 positioned radially opposite the first drive tab 594.

In some embodiments, the worm wheel 512 may include one or more corresponding drive tabs 518. For example, the worm wheel 512 may include a first drive tab 518 and a second drive tab 518 positioned radially opposite the first drive tab 518. The drive tabs 518 of the worm wheel 512 may extend radially inward from an inner surface of the worm wheel 512 toward a central axis of the worm wheel 512. The drive tabs 518 of the worm wheel 512 may be positioned between the first and second drive tabs 594 of the central axle 590. In some embodiments, one or more of the drive tabs 594 of the central axle 590 engages one or more of the drive tabs 518 of the worm wheel 512 (e.g., contacts, abuts, connects to, etc.) to transmit a rotational force of the worm wheel 512 to the central axle 590.

The drive mechanism of the digit 500 may include a spring 503 (e.g., a torsion spring). The spring 503 may be coupled to (e.g., circumferentially surround) an axially extending member 502 that extends axially along the central axis of the worm wheel 512 and/or central axle 590. The spring 503 may be configured to rotationally bias the worm wheel 512 in an angular direction to maintain the relative positions of the central axle 590 and the worm wheel 512. For example, the spring 503 may include a flange 508 that extends further radially outward than the rest of the spring 503. The flange 508 may engage one of the drive tabs 518 of the worm wheel 512. For example, in some embodiments, the worm wheel 512 and the central axle 590 are positioned such that one of the drive tabs 594 of the central axle 590 abuts a first surface of one of the drive tabs 518 of the worm wheel 512 and the flange 508 abuts a second surface of the drive tab 518 opposite the first surface of the drive tab 518. This configuration enables the rotational force of the worm wheel 512 to be transmitted to the central axle 590 while maintaining the relative positions of the worm wheel 512 and the central axle 590. This configuration also allows the digit 500 to be closed independent of the drive mechanism of the digit 500, as further described below.

In some embodiments, the digit 500 may be opened and/or closed with or without utilizing the actuator 504. For example, the digit 500 can have a worm wheel driven movement mode (e.g., driven by the actuator 504) and a manual movement mode (e.g., driven by an external force). When the digit 500 is in an open position, application of an external force on the digit 500 in a closing direction may cause the digit 500 to fold to a closed position. In some embodiments, in the manual movement mode, unlike in the worm wheel driven movement mode, the actuator 504 does not drive the worm wheel 512. For example, in the manual movement mode, the actuator 504 and the worm wheel 512 remain stationary. In the manual movement mode, the central axle 590 rotates in response to the application of an external force to the digit 500 while the worm wheel 512 remains stationary because the spring flange 508 allows for rotational movement when its spring biasing force is overcome. The rotation of the central axle 590 may cause the segments 520, 530, 540 of the digit 500 to rotate to a closed position. In the manual movement mode, the projections 518 of the worm wheel 512 may limit the range of rotation of one or more of the drive tabs 594 of the central axle 590 and therefore the range of rotation of the central axle 590. The spring 503 may rotate and store energy due to the manual movement of the digit 500 to the closed position due to the application of an external force to the digit 500. In some embodiments, when the external force is removed from the digit 500, the spring 503 may use the stored potential energy to rotate and cause the digit 500 to return to the open position.

The manual movement mode of the digit 500 can advantageously serve as a mechanical protection system when external forces act on the digit 500, such as when a user falls on the digit 500 or applies pressure to the digit 500 to get up from a chair, etc. The manual closure of the digit 500 may allow the external load to be supported by components of the digit 500 other than the drive mechanism (e.g., gearbox). This can prevent damage that may otherwise have been caused to the drive mechanism of the digit 500.

Figure 10:
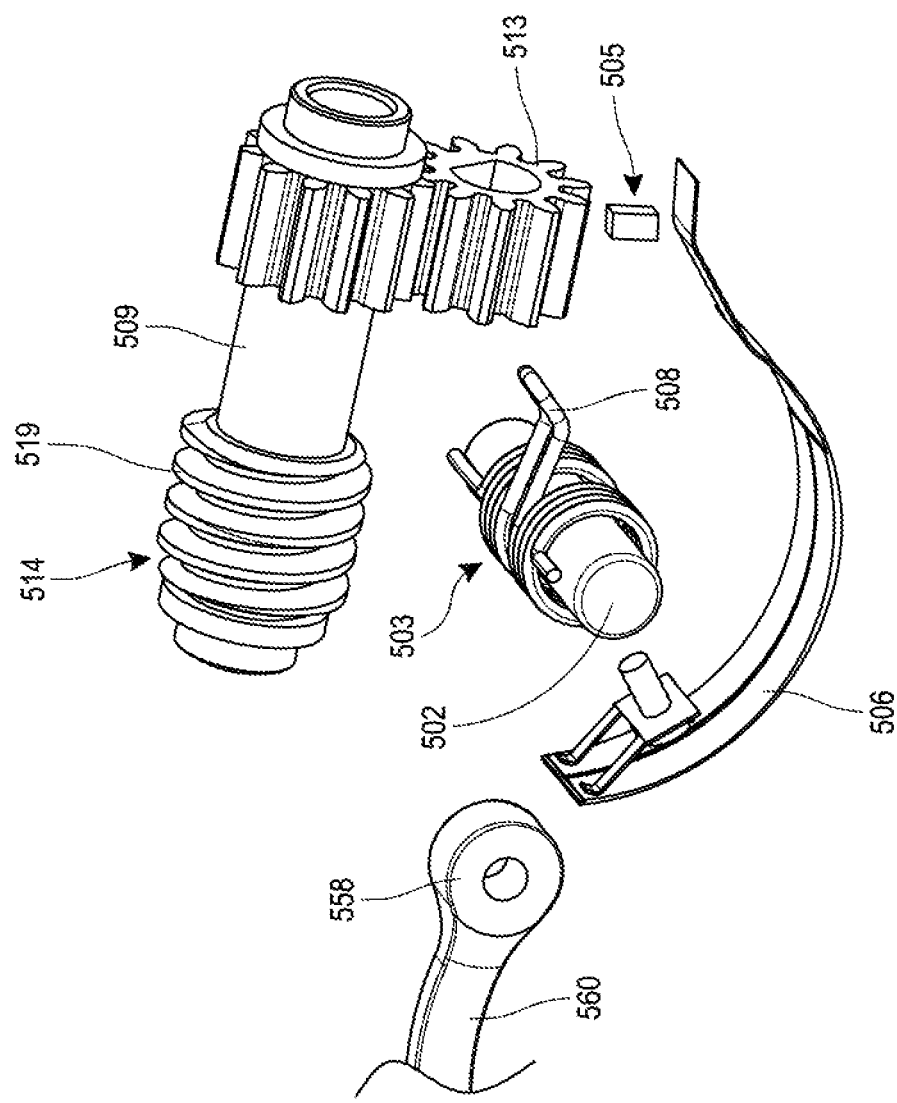
FIG. 10 is a perspective view of the actuator of FIGS. 9A-9C with some components removed for clarity.

FIG. 10 illustrates the positions of encoders 505, 506 within the digit 500. In some embodiments, the digit 500 includes a plurality of encoders 505, 506 mounted to the gearbox. For example, in some embodiments, the digit 500 includes a first type of encoder for the worm wheel driven movement mode and a second type of encoder for the manual movement mode. As shown, the digit 500 may include a potentiometer strip encoder 506 and a magnetometer encoder 505. The potentiometer strip encoder 506 may be coupled to the worm wheel 512. The magnetometer encoder 505 may be positioned between the potentiometer strip encoder 506 and the pinion gear 513. The potentiometer strip encoder 506 may measure the position of the digit 500 by measuring the absolute position of the motor drive. The magnetometer encoder 505 may be an absolute magnetic hall effect encoder. The magnetometer encoder 505 may measure the position of the digit 500 by measuring the degree of rotation of a diametrically magnetized axial magnet disposed within the axially extending member 502 at the center of the central axle 590.

Figure 11:
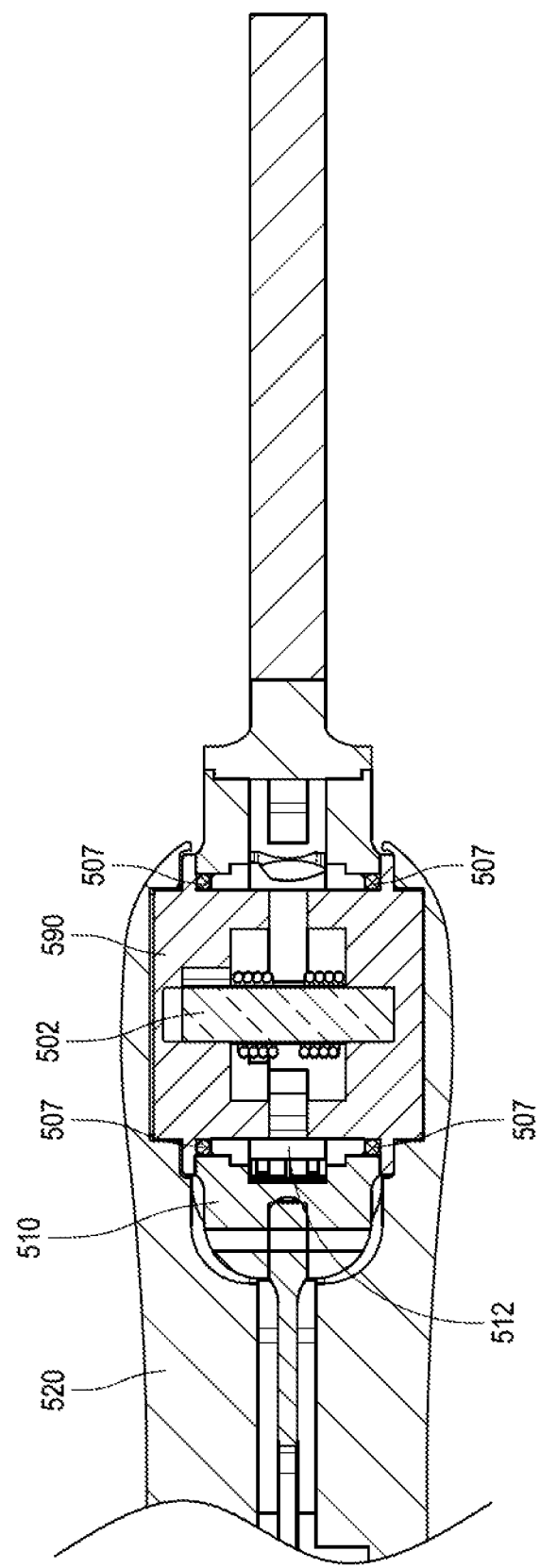
FIG. 11 is a cross-sectional view of a portion of the prosthetic digit of FIGS. 8A-8B.

FIG. 11 is a cross-sectional view of a portion of the digit 500 illustrating waterproof seals 507 within the digit 500. In some embodiments, the digit 500 may be waterproof (e.g., rated IP68). The digit 500 may include seals 507, such as O-ring seals, lip seals, and/or other dynamic seals, to seal the components within the central axle 590 from water ingress. For example, the seals 507 may be positioned in gaps between the central axle 590 and the mount 510.

Various modifications to the implementations described in this disclosure can be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A prosthetic digit comprising:
   a mount fixedly attached to a palm;
   a proximal segment, a middle segment, and a distal segment, with the proximal segment rotatably attached to the mount at a first pivot, and the middle segment rotatably attached to the proximal and distal segments;
   a proximal link rotatably attached to the mount and rotatably attached to the middle segment at a second pivot;
   a distal link rotatably attached to the proximal link and rotatably attached to the distal segment at a third pivot; and
   an actuator coupled with the mount and the proximal segment, the actuator comprising a worm wheel disposed within the mount, the worm wheel configured to cause the proximal segment to rotate about the first pivot, wherein rotation of the proximal segment about the first pivot causes the middle and distal segments to rotate.

2. The prosthetic digit of claim 1, wherein the mount comprises a proximal end and a distal end, the distal end is rotatably attached to the proximal link, and the first pivot is located between the proximal and distal ends.

3. The prosthetic digit of claim 1, wherein the proximal link comprises a proximal end and a distal end, the proximal end is rotatably attached to the mount, the distal end is rotatably attached to the distal link, and the second pivot is located between the proximal and distal ends.

4. The prosthetic digit of claim 1, wherein rotation of the proximal segment about the first pivot causes rotation of the proximal link.

5. The prosthetic digit of claim 1, wherein the proximal link comprises a dogleg.

6. The prosthetic digit of claim 1, wherein rotation of the proximal segment causes the proximal, middle, and distal segments to rotate simultaneously.

7. The prosthetic digit of claim 1, wherein the palm is a prosthetic palm.

8. The prosthetic digit of claim 1, wherein the worm wheel comprises a first mating portion configured to mate with a second mating portion of an inner surface of the proximal segment, wherein rotation of the first mating portion causes the proximal segment to rotate.

9. The prosthetic digit of claim 8, wherein an application of an external force to the digit causes the worm wheel to rotate.

10. The prosthetic digit of claim 9, further comprising a spring configured to rotationally bias the worm wheel about an axis of rotation of the worm wheel, wherein a removal of the external force causes the digit to return to a neutral position.

11. The prosthetic digit of claim 1, wherein the actuator comprises a potentiometer strip encoder and a magnetometer encoder.

12. The prosthetic digit of claim 1, further comprising a worm gear in mechanical communication with the worm wheel, wherein the prosthetic digit in a fully extended position extends along a longitudinal axis, and wherein the worm gear is configured to rotate about an axis that is parallel to the longitudinal axis.

13. The prosthetic digit of claim 12, further comprising a motor in mechanical communication with a shaft of the worm gear, the motor configured to rotate an output shaft of the motor to cause the shaft of the worm gear to rotate, and wherein the shaft of the worm gear is off-axis relative to the motor output shaft.

14. A prosthetic hand comprising:
a prosthetic palm; and
a prosthetic digit comprising:
a mount fixedly attached to the prosthetic palm;
a proximal segment, a middle segment, and a distal segment, with the proximal segment rotatably attached to the mount at a first pivot, and the middle segment rotatably attached to the proximal and distal segments;
a proximal link rotatably attached to the mount and rotatably attached to the middle segment at a second pivot;
a distal link rotatably attached to the proximal link and rotatably attached to the distal segment at a third pivot; and
an actuator coupled with the mount and the proximal segment, the actuator comprising a worm wheel disposed within the mount, the worm wheel configured to cause the proximal segment to rotate about the first pivot, wherein rotation of the proximal segment about the first pivot causes the middle and distal segments to rotate.

15. The prosthetic hand of claim 14, wherein the mount comprises a proximal end and a distal end, the distal end is rotatably attached to the proximal link, and the first pivot is located between the proximal and distal ends.

16. The prosthetic hand of claim 14, wherein the proximal link comprises a proximal end and a distal end, the proximal end is rotatably attached to the mount, the distal end is rotatably attached to the distal link, and the second pivot is located between the proximal and distal ends.

17. The prosthetic hand of claim 14, wherein rotation of the proximal segment about the first pivot causes rotation of the proximal link.

18. The prosthetic hand of claim 14, wherein the proximal link comprises a dogleg.

19. A method for operating a prosthetic digit having proximal, middle, and distal segments, the method comprising:
actuating a motor;
rotating a worm wheel in response to actuation of the motor;
rotating the proximal segment in response to rotation of the worm wheel;
rotating a proximal link relative to a mount that is fixed with respect to a palm in response to rotation of the proximal segment, wherein the proximal link is rotatably attached to the middle segment of the prosthetic digit;
rotating the middle segment relative to the proximal segment in response to rotating the proximal link;
rotating a distal link in response to rotation of the middle segment, wherein the distal link is rotatably attached to the distal segment of the prosthetic digit; and
rotating the distal segment relative to the middle segment in response to rotating the distal link.

20. The method of claim 19, further comprising rotating the proximal segment in response to rotation of the worm wheel via a connection comprising a drive key and recess.

21. The method of claim 19, further comprising causing the distal segment to rotate relative to the middle segment via the distal link rotationally coupled with the proximal link.

22. The method of claim 19, further comprising rotating a worm gear, in response to actuation of the motor, to thereby cause the worm wheel to rotate.

* * * * *